US007408039B2

(12) United States Patent
Sykes et al.

(10) Patent No.: US 7,408,039 B2
(45) Date of Patent: Aug. 5, 2008

(54) KITS FOR TREATMENT OF HEMATOLOGIC DISORDERS

(75) Inventors: Megan Sykes, Boston, MA (US); Thomas R. Spitzer, Andover, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/374,302

(22) Filed: Feb. 25, 2003

(65) Prior Publication Data

US 2003/0157077 A1 Aug. 21, 2003

Related U.S. Application Data

(63) Continuation of application No. 09/191,970, filed on Nov. 13, 1998, now Pat. No. 6,558,662.

(60) Provisional application No. 60/073,230, filed on Nov. 14, 1997.

(51) Int. Cl.
*C07K 16/00* (2006.01)
*G01N 33/53* (2006.01)
*A01N 25/00* (2006.01)

(52) U.S. Cl. ............... 530/387.1; 530/387.9; 435/810; 514/885

(58) Field of Classification Search ................ 435/7.1, 435/810; 514/885
See application file for complete search history.

(56) References Cited

U.S. PATENT DOCUMENTS

| 4,281,061 | A | * | 7/1981 | Zuk et al. ................. 435/7.9 |
| 4,683,195 | A | | 7/1987 | Mullis et al. ............... 435/6 |
| 5,004,681 | A | | 4/1991 | Boyse et al. ................ 453/2 |
| 5,192,553 | A | | 3/1993 | Boyse et al. ............... 424/529 |
| 5,484,612 | A | * | 1/1996 | Brown ...................... 424/649 |
| 5,635,156 | A | | 6/1997 | Ildstad .................... 424/1.49 |
| 5,730,979 | A | | 3/1998 | Bazin et al. |
| 5,834,266 | A | | 11/1998 | Crabtree et al. .......... 435/172.3 |

FOREIGN PATENT DOCUMENTS

| WO | WO 89/04168 | 5/1989 |
| WO | WO 93/13785 | 7/1993 |
| WO | WO 94/20619 | 9/1994 |
| WO | WO 95/03062 | 2/1995 |
| WO | WO 95/11692 | 5/1995 |
| WO | WO 95/26740 | * 10/1995 |
| WO | WO 96/06165 | 2/1996 |
| WO | WO 97/41863 | 11/1997 |
| WO | WO 98/20932 | 5/1998 |

OTHER PUBLICATIONS

Maraninchi et al. Lancet, 1987, vol. 2 pp. 175-178.*
Atkinson et al., Bone Marrow Transplantation, 1987, 2 pages 79-84.*

Aizawa, S. et al., "Graft-Versus-Leukemia Effect in MHC-Compatible and -Incompatible Allogenic Bone Marrow Transplantation of Radiation-Induced, Leukemia-Bearing Mice", *Taransplantation*, 52:885-9 (1991).
Anasetti, C. et al., "Effect of HLA Compatibility on Engraftment of Bone Marrow Transplants in Patients with Leukemia of Lymphoma", *The N. E. Journal of Med.*, 320:197-204 (1989).
Baum, C. et al., "Isolation of a candidate human hematopoietic stem-cell population", *Proc. Natl. Acad. Sci. USA*, 89:2804-8 (1992).
Baurmann, H. et al., "Kinetics of the Graft-Versus-Leukemia Response After Donor Leukocyte Infusions for Relapsed Chronic Myeloid Leukemia After Allogeneic Bone Marrow Transplantation", *Blood*, 92:3582-3590 (1998).
Chopra, R. et al., "Autologous Versus Allogenic Bone Marrow Transplantation for Non-Hodgkin's Lymphoma: A Case-Controlled Analysis of the European Bone Marrow Transplant Group Registry Data", *J. Clin. Onc.*, 10:1690-95.
Clift, R. et al., "Histoincompatible Bone Marrow Transplants in Humans", *Ann. Rev. Immunol.*, 5:43-64 (1987).
Emerson, S., "Ex Vivo Expansion of Hematopoietic Prcursors, Progenitors, and Stem Cells: The Next Generation of Cellular Therapeutics", *Blood*, 87:3082-88 (1996).
Fleischhauer, K. et al., Bone Marrow-Allograft Rejection by T Lymphocytes Recognizing a Single Amino Acid Difference in HLA-B44 (1990).
Giralt, S. et al., Engraftment of Allogeneic Homeopoietic Progenitor Cells with Purine Analog-Containing Chemotherapy: Harnessing Graft-Versus-Leukemia without Myeloablative Therapy, *Blood*, 89:4531-36 (1997).
Giralt, S. et al., "Induction of graft-versus-leukemia (GVL)as primar treatment of chronic myelogenous leukemia (CML)", *Blood*, 90:418a (1997).
Henslee-Downey, P. et al., "Combined In Vitro and In Vivo T Lymphocyte Depletion for the Control of Graft-Versus-Host Disease Following Haploidentical Marrow Transplant", *Transplantation*, 61:738-745 (1996).
Henslee-Downey, P. et al., "Use of Partially Mismatched Related Donors Extends Access to Allogeneic Marrow Transplant", *Blood*, 89:3864-3872 (1997).
Ilstad, S. et al., "Effect of Selective T Cell Depletion of Host and/or Donor Bone Marrow on Lymphopoietic Repopulation, Tolerance, and Graft-ve-Host Disease in Mixed Allogeneic Chimeras (B10+B10.D2−B10)", *J. Immunology*, 136:28-33 (1986).
Ilstad, S. et al., "Reconstitution with syngeneic plus allogeneic or xenogeneic bone marrow leads to specific acceptance of allografts or xenografts", *Nature*, 307:168-70 (1984).
Johnson, B. D. et al., "Delayed infusion of normal donor cells after MHC-matches bone marrow transplantation provides and antileukemia reaction without graft-versus-host disease", *Bone Marrow Transplantation*, 11:329-.

(Continued)

*Primary Examiner*—Michail A Belyavskyi
(74) *Attorney, Agent, or Firm*—Choate, Hall & Stewart, LLP

(57) ABSTRACT

The inventors have discovered that hematologic disorders, e.g., both neoplastic (hematologic cancers) and non-neoplastic conditions, can be treated by the induction of mixed chimerism using myeloreductive, but not myeloablative, conditioning. Methods of the invention reduce GVHD, especially GVHD associated with mismatched allogeneic or xenogeneic donor tissue, yet provide, for example, significant graft-versus-leukemia (GVL) effect and the like.

13 Claims, 2 Drawing Sheets

OTHER PUBLICATIONS

Jones, R. et al., "Evidence of a Graft-Versus-Lymphoma Effect Associated With Allogeneic Bone Marrow Transplantation", *Blood*, 77:649-53 (1991).

Kawai, T. et al., "Mixed Allogeneic Chimerism and Renal Allogrtft Tolerance in Cynomolgus Monkeys", *Transplantation*, 59:256-62 (1995).

Khouri, I. et al., "Transplant-Lite: Induction of Graft-Versus-Malignancy Using Fludarabine-Based Nonablative Chemotherapy and Allogeneic Blood Progenitor-Cell Transplantation os Treatment for Lymphoid Malignancies", *J. Clinical Oncology*, 16:2817-24 (1998).

Kolb, H. et al., "Adoptive Immunotherapy in Canine Chimeras", *Transplantation*, 63:430-436 (1997).

Lansdorp, P.M. et al., "Selective Expression of CD45 Isoforms on Functional Subpopulations of $CD34^+$Hemopoietic Cells from Human Bone Marrow", *J. Exp. Med.*, 172:363-66 (1990).

Lapierre, Y. et al., "The gel test: a new way to detect red cell antigen-antibody reactions", *Transfusion*, 30:109-113 (1990).

Lenschow, D. et al., "Long-Term Survival of Xenogeneic Pancreatic Islet Grafts Induced by CTLA4Ig", *Science*, 257:789-792 (1992).

Lundberg, J. et al., "Allogeneic Bone Marrow Transplantation for Relapsed and Refractory Lymphoma Using Genotypically HLA-Identical and Alternative Donors", *J. Clin. Oncol.*, 9:1848-59 (1991).

Mackinnon, S. et al., "Adoptive Immunotherapy Evaluating Escalating Doses of Donor Leukocytes for Relapse of Chronic Myeloid Leukemia After Bone Marrow Transplantation: Separation of Graft-Versus Leukemia Response From Graft-Versus-Host Disease", *Blood*, 86:1261-1268 (1995).

Nakao, S. et al., "Analysis of late graft failure after allogeneic bone marrow transplantation: detection of residual host cell using amplification of variable number of tandem repeats loci", *Bone Marrow Trans.*, 9:107-111 (1992).

Nikolic, B. et al., "Bone marrow chimerism and transplantation tolerence", *Current Opinion in Immun.*, 9:634-40 (1997).

Nikolic, B. et al., "Mixed Hematopoietic, Chimerism and Transplantation Tolerance", *Immun. Res.*, 16/3:217-28 (1997).

O, Rielly, R. J. et al., "Transplantation of Marrow Depleted T Cells b Soybean Lectin Agglutination and E-Rosette Depletion: Major Histocompatibility Complex-Related Graft Reisstance in Leukemic Transplant Recipients", *Transplantation Proceedings*, 17:455-59 (1985).

Petzer, A. et al., "Self-renewal of primitive human hematopoietic cells (long-term-culture-initiating cells) in vitro and their expansion in defined medium", *Proc. Natl. Acad. Sci. USA*, 93:1470-74 (1996).

Porter, D.L. et al., "Adoptive Immunotherapy with donor mononuclear cell infusions to treat relapse of acute leukemia of myelodysplasia after allogeneic bone marrow transplantation", *Bone Marrow Transplantation*, 18:975-.

Preffer, F., "Flow Cytometry", *Diagnostic Immunopathology, Second Edition*, Raven Press, Ltd., New York, pp. 725-749 (1995).

Ratanatharathorn, V. et al., "Prospective Comparative trial of Autologous Versus Allogeneic Bone Marrow Transplantation in Patients With Non-Hodgkin's Lymphoma", *Blood*, 84:1050-55 (1994).

Sato, N. et al., "Purification of Human Marrow Progenitor Cells and Demonstration of Direct Action of Macrophage Colony-Stimulating Factor on Colony-Forming Unit-Macrophage", *Blood*, 78:967-74 (1991).

Schwartz, D. et al., "Startegy to Detect Chimerism in Allogeneic Bone Marrow Transplant Recipients by PCR-Amplification Fragment Length Polymorphism Analysis of Microsatellite Polymorphisms", *Vox Sanguinis*, 68:139-43 (1995).

Sharabi, Y. et al., "Mixed Chimerism and Permanent Specific Transplantation Tolerance Induced By a Nonlethal Preparative Regimen", *J. Exp. Med.*, et al., 169:493-502 (1989).

Slavin, S. et al., "Nonmyeloablative Stem Cell Transplantation and Cell Therapy as an Alternative to Conventional Bone Marrow Transplantation With Lethal Cytoreduction for the Treatment of Malignant and Nonmalignant Hematologic Diseases", *Blood*, 91:756-763 (1998).

Smith, C. et al., "Purification and Partial Characterization of a Human Hematopoietic Precursor Population", *Blood*, 77:2122-28 (1991).

Spitzer, T. et al., "Clinical remission of refractory non-Hodgkin's lymphoma induced by allogeneic bone marrow transplantation (BMT) with mixed chimerism in non-myeloblated recipients", *Blood*, 90:418a (1997).

Sprent, J. et al., "Role of T Cell Subsets in Lethal Graft-Versus-Host Disease (GHVD) Directed to Class I Versus Class II H-2 Differences", *J. Exp. Med.*, 167:556-569 (1988).

Storb, R. et al., "Stable Mixed Hematopoietic Chimerism in DLA-Identical Littermate Dogs Given Sublethal Total Body Irradiation Before and Pharmacological Immunosuppression After Marrow Transplantation", *Blood*, 89:3048-3054 (1997).

Sykes, M. et al., "Genetic Analysis of the Anti-Leukemic Effect of Mixed Allogeneic Bone Marrow Transplantation", *Transplantation Proceedings*, 21:3022-24 (1989).

Sykes, M. et al, "Graft-Versus-Host-Related Immunosuppression is Induced in Mixed Chimeras Ny Alloresponses Against Either Host or Donor Lymphohematopoietic Cells", *J. Exp. Med.*, 168:2391-96(1988).

Sykes, M. et al., "Graft-versus-leukemia effect using mixed allogeneic bone marrow transplantation", *Bone Marrow Transplantation*, 4:465-474 (1989).

Sykes, M. et al., "Induction of high levels of allogeneic hematopoietic reconstitution and donor-specific tolerance without myelosuppressive conditioning", *Nature Medicine*, 3:783-787 (1997).

Sykes, M. et al., "Mixed lymphohaemopoietic chimerism and graft-versus-lymphoma effects after non-myeloablative therapy and HLA-mismatched bone-marrow transplantation", *The Lancet*, 353:1755-59 (1999).

Sykes, M. et al, "Protection From Graft-Versus-Host Disease in Fully Allogeneic Chimeras by Prior Administration of T Cell-Depleted Syngeneic Bone Marrow", *Transplantation*, 46:327-30 (1988).

Sykes, M. et al., "Tolerance Induction for Xenotransplantation", *World J. Surg.*, 21:932-938 (1997).

Turka, L. et al., "T-cell activation by the CD28 ligand B7 is required for cardiac allograft rejection in vivo", *Proc. Natl. Acad. Sci. USA*, 89:11102-05 (1992).

Udomsakdi, C. et al., "Characterization of Primitive Hematopoietic Cells in Normal Human Peripheral Blood", *Blood*, 80:2513-21 (1992).

Udomsakdi, C. et al., "Separation of Functionally Distinct Subpopulation of Primitive Human Hematopoietic Cells using Rhodamine-123", *Exp. Hematol.*, 19:338-42 (1991).

Verdonck, L. et al., "Allogeneic Versus Autologus Bone Marrow Transplantation to Refractory and Recurrent Low-Grade Non-Hodgkin's Lymphoma", *Blood*, 90:4201-05 (1997).

Xun, C. et al., "Effect of Total Body Irradiation, Busulfan-Cyclophosphamide, or Cyclophosphamide Conditioning on Inflammatory Cytokine Release and Development of Acute and Chronic Graft-Versus-Host Disease in H-2-Incompatible Transplanted SCID Mice", *Blood*, 83:2360-67 (1994).

Zandstra, P. et al., "Expansion of Hematopoietic Progenitor Cell Populations in Stirred Suspension Bioreactors of Normal Human Bone Marrow Cells", *Bio/Technology*, 12:909-914 (1994).

Zhao, Y. et al., "Pig MHC Mediates Positive Selection of Mouse $CD4^+$T Cells with a Mouse MHC-Restricted TCR in Pig Thymus Grafts", *J. Immun.*, 161:1320-26 (1998).

Bär et al.; "Donor Leukocyte Infusions for Chronic Myeloid Leukemia Relapsed After Allogeneic Bone Marrow Transplantation", Journal of Clinical Oncology 11(3): 513-519 (Mar. 1993).

Johnson et al.; "Delayed Infusion of Normal Donor Cells after MHC-matched Bone Marrow Transplantation Provides an Antileukemia Reaction Without Graft-versus-host disease",Bone Marrow Transplantation 11:329-336 (1993).

* cited by examiner

US 7,408,039 B2

KITS FOR TREATMENT OF HEMATOLOGIC DISORDERS

This application claims the benefit of priority under 35 U.S.C. § 120 and is a continuation of Ser. No. 09/191,970, filed Nov. 13, 1998, now U.S. Pat. No. 6,558,662 now allowed; which is a continuation of U.S. provisional application 60/073,230, filed Nov. 14, 1997, both of which are hereby incorporated by reference in their entireties.

GOVERNMENT FUNDING

The work herein was supported by a grant from the National Institutes of Health. The government may have certain rights in the invention.

BACKGROUND OF THE INVENTION

The invention relates to the treatment of hematologic disorders, e.g., disorders characterized by unwanted cells of hematopoietic origin, e.g., hematologic cancers.

Bone marrow transplantation (BMT) has yet to realize its full potential for the treatment of hematologic malignancies. A major obstacle to further advancement is graft-versus-host disease (GVHD), which has been prevented by removing T cells from the donor marrow. Unfortunately, T cell depletion has been associated with increased rates of engraftment failure and leukemic relapse. Despite improvements in pharmacologic GVHD prophylaxis, severe acute and chronic GVHD are still major complications of HLA-matched sibling bone marrow transplantation. Immunosuppressive drugs used for GVHD prophylaxis may also increase the relapse rate for certain types of leukemia. The patients receiving allogeneic BMT are, nevertheless, a fortunate select group: most patients do not have an HLA-matched sibling or a phenotypically matched unrelated donor, and therefore do not have the option of BMT. Attempts to perform BMT between strongly HLA-mismatched donor-recipient pairs have been associated with a prohibitively high incidence of severe GVHD and of failure of engraftment. Furthermore, a large fraction of leukemias and lymphomas afflict older patients who are more prone to the development of GVHD than are younger persons, and who therefore are not generally considered candidates for BMT, despite the lack of other curative options.

SUMMARY OF THE INVENTION

The inventors have discovered that hematologic disorders, e.g., both neoplastic (hematologic cancers) and non-neoplastic conditions, can be treated by the induction of mixed chimerism in the absence of whole body irradiation (total myeloablation protocols) or other myeloablative treatment. Methods of the invention reduce GVHD, especially GVHD associated with mismatched allogeneic or xenogeneic donor tissue, yet provide significant graft-versus-leukemia (GVL) effect and the like.

Certain embodiments of the subject methods also feature preparative regimens which minimize or eliminate the need for myeloablative treatment, e.g., hematopoietic space-creating irradiation, especially, preparative whole body irradiation.

One aspect of the present invention provides a method for treating a subject having a hematologic disorder comprising: (i) administering a myeloreductive non-myeloablative treatment to the subject in sufficient amount such that mixed hematopoietic chimerism can be induced in the subject, and (ii) introducing into the subject, allogeneic donor hematopoietic stem cells (donor stem cells) to form chimeric bone marrow in the subject.

In certain embodiments, the myeloreductive treatment includes treating the subject with an immunosuppressant regimen, prior to introduction of the donor stem cells, in an amount sufficient to prevent rejection of the donor stem cells.

Likewise, the method can include a further step of treating the subject with an immunosuppressant regimen, after introduction of the donor stem cells, in an amount sufficient to prevent a graft-versus-host response mediated by the donor stem cells.

Such immunosuppressant regimens can include, independently for pre- and post-transplantation is both are carried out, a treatment of the subject which inactivates and/or depletes host T-lymphocytes and/or natural killer (NK) cells in the subject. For example, the immunosuppressant regimen includes treatment with T cell-depleting anti-CD4 and/or CD8 antibodies, such as anti-thymocyte globulin (ATG), OKT3 (Orthoclone OKT3 monoclonal antibody, Ortho Pharmaceutical Corp), LO-CD2a (U.S. Pat. No. 5,730,979), or Minnesota anti-lymphoblast globulin (MALG). Preferably, the immunosuppressant regimen, both before and after transplantation, includes administration of ATG.

A cell line which produces the monoclonal antibody LO-CD2a (also known as BTI-322) was deposited on Jul. 28, 1993, at the American Tissue Culture Collection, 10801 University Blvd., Manassas, Va. 20110-2209, and was given ATCC accession number 11423. This hybridoma is being maintained under the terms of the Budapest Treaty.

Moreover, the immunosuppressant regimen can include treatment with thymic irradiation. Preferably, the pre-transplantation immunosuppressant conditioning includes administration of ATG and thymic irradiation.

In other embodiments, the immunosuppressant regimen includes treatment with one or more of a macrolide immunosuppressant, azathioprine, steroids (e.g., prednisone, methyl prednisolone), sub-lethal nonmyleoablative irradiation of lymphocyte-containing tissue, or costimulatory blocking agents (e.g., anti-CD40 ligands, CTLA4Ig fusion proteins, see, e.g., Lenschow et al., (1992) *Science* 257:789; and Turka et al., (1992) *PNAS* 89:11102).

In certain embodiments, the myeloreductive treatment includes treating the subject, prior to introduction of the donor stem cells, with an cytoreductive agent selected from one or more of alkylating agents (e.g., nitrogen mustards [such as mechloretamine], cyclophosphamide, melphalan and chlorambucil), alkyl sulphonates (e.g., busulphan), nitrosoureas (e.g., carmustine, lomustine, semustine and streptozocine), triazenes (e.g., dacarbazine), antimetabolites (e.g., folic acid analogs such as methotrexate), pyrimidine analogs (e.g. fluorouracil and cytarabine), purine analogs (e.g., fludarabine, idarubicin, cytosine arabinoside, mercaptopurine and thioguanine), vinca alkaloids (e.g., vinblastine, vincristine and vendesine), epipodophyllotoxins (e.g., etoposide and teniposide), antibiotics (e.g., dactinomycin, daunorubicin, doxorubicin, bleomycin, plicamycin and mitomycin), dibromomannitol, deoxyspergualine, dimethyl myleran and thiotepa.

Preferably, the myeloreductive treatment includes treating the subject with cyclophosphamide.

Preferably, the pre-transplantation conditioning includes administration of ATG and cyclophosphamide, and thymic irradiation. Preferably the cyclophosphamide, or other cytoreductive agents, are substantially cleared from the patient so as not inhibit proliferation of the transplanted stem cells.

An important use of the subject method is for allogeneic transplantation of donor stem cells which are mismatched, with respect to the subject, at one or more HLA class II antigens.

Another important use of the subject method is for allogeneic transplantation of donor stem cells which are mismatched, with respect to the subject, at two or more HLA antigens (either HLA class I or II or both).

In preferred embodiments, the donor stem cells are provided as allogeneic bone marrow, mobilized peripheral blood cells, or cord blood cells.

The donor stem cells, in some instances, can be expanded ex vivo for transplantation.

In preferred embodiments, the donor stem cells are from the same species as the subject. However, the present application also specifically contemplates that the donor stem cells are xenogeneic stem cells from a different species than the subject. In xenogeneic methods, the subject is a mammal, preferably a primate and more preferably a human. The donor mammal can be, by way of example, a swine, e.g., a miniature swine, or a nonhuman primate. In xenogeneic methods the donor of stem cells and the donor of leukocytes need not be the same individual but can be from different individuals which are MHC matched or highly inbred, e.g., inbred miniature swine which are MHC matched.

In preferred embodiments, the subject is a human, and even more preferably, the subject is a human and donor stem cells are from another human.

The methods of the present invention can be used to treat a wide range of hematologic disorders, including neoplastic proliferation of hematopoetic cells, such as lymphoblastic leukemia, myelogenous leukemia, Hodgkin's lymphoma, Non-Hodgkin's lymphoma and myelodysplastic syndrome. As described herein, the subject method can be used to treat hematologic disorders which are refractory to chemotherapy, such a chemorefactory Non-Hodgkin's lymphoma.

In other embodiments, the subject method can be used to treat hematologic disorders which are non-malignant, such as erythrocyte abnormalities or immune system disorders. For example, the instant method can be used to treat hemoglobinopathies, e.g., sickle cell anemia, aplastic anemia or thalassemia. The subject method also can be used as part of a treatment regimen for autoimmune disorders as well as immunodeficiencies.

In several embodiments, particularly where little, and preferably no GVHD is detected post-transplantation (e.g., at least 14 days, and more preferably at least 25, 30 or even 35 days), the subject method includes the further step of administering allogeneic donor leukocytes to the subject after introduction of the donor stem cells. The administration of donor leukocytes should be delayed sufficiently from the time of any hematopoietic space creating treatment such that the level of pro-inflammatory cytokines induced by the space creating treatment has subsided sufficiently to reduce or substantially eliminate GVHD from the donor leukocytes.

The subject method can also include the management of GVHD responses post-transplantation by administration of immunosuppressants, or by use of engineered stem cells which give rise to small molecule ablatable T cells or other hematopoietic cells. See, for example, U.S. Pat. No. 5,834,266.

In another aspect, the invention features a method of treating a non-neoplastic disorder or a hemoglobinopathy, e.g., sickle cell anemia, aplastic anemia, thalassemia Thus, in one preferred embodiment, the subject method comprises: (i) identifying a patient having a neoplastic hematopoetic disorder, (ii) administering a myeloreductive treatment to the subject in sufficient amount such that mixed hematopoietic chimerism can be induced in the subject, and (iii) introducing into the subject, allogeneic donor hematopoietic stem cells (donor stem cells) to form stable mixed chimeric bone marrow in the subject.

In another preferred embodiment, the subject method comprises: (i) identifying a patient having a neoplastic hematopoetic disorder, (ii) administering a myeloreductive treatment to the subject in sufficient amount such that mixed hematopoietic chimerism can be induced in the subject, and (iii) introducing into the subject, allogeneic donor hematopoietic stem cells (donor stem cells) to form mixed chimeric bone marrow in the subject, wherein the donor stem cells are mismatched, with respect to the patient, at one or more class II HLA antigens.

In still another preferred embodiment, the subject method comprises: (i) identifying a patient having a neoplastic hematopoetic disorder, (ii) administering a myeloreductive treatment to the subject in sufficient amount such that mixed hematopoietic chimerism can be induced in the subject, and (iii) introducing into the subject, allogeneic donor hematopoietic stem cells (donor stem cells) to form mixed chimeric bone marrow in the subject, wherein the donor stem cells are mismatched, with respect to the patient, at two or more HLA antigens, e.g., class I and/or class II.

In yet another preferred embodiment, the subject method comprises: (i) identifying a patient having a neoplastic hematopoetic disorder, (ii) administering a myeloreductive treatment to the subject in sufficient amount such that mixed hematopoietic chimerism can be induced in the subject, (iii) introducing into the subject, allogeneic donor hematopoietic stem cells (donor stem cells) to form mixed chimeric bone marrow in the subject, and (iv) administering a post-transplantation immunosuppression regimen for suppressing or depleting T-cells in the transplanted donor stem cells.

In yet another preferred embodiment, the subject method comprises: (i) identifying a patient having a neoplastic hematopoetic disorder, (ii) administering a pre-transplantation conditioning to the subject in sufficient amount such that mixed hematopoietic chimerism can be induced in the subject, which pre-transplantation conditioning includes treating the cells with cyclophosphamide, ATG and thymic irradiation in an amount sufficient to reduce rejection of transplanted donor stem cells; and (iii) introducing into the subject, allogeneic donor hematopoietic stem cells (donor stem cells) to form mixed chimeric bone marrow in the subject, and (iv) administering ATG to the subject post-transplant for suppressing or depleting T-cells in the transplanted donor stem cells.

Another aspect of the present invention relates to the use of donor allogeneic stem cells in the manufacture of a medicament for the treatment of a hematologic disorder, wherein the medicament administered to a patient conditioned with myeloreductive non-myeloablative treatment, and in an amount sufficient to form chimeric bone marrow in the subject.

Still another aspect of the present invention provides a kit for allogeneic hematopoietic stem cell transplantation. The kit includes cyclophosphamide in an amount sufficient to reduce rejection of transplanted donor stem cells when administered to a patient pre-transplantation, and ATG in an amount sufficient to reduce rejection of transplanted donor stem cells when administered to a patient pre-transplantation and suppress T-cells in transplanted donor stem cells. The kit may also include a labeled antibody for detecting leukocytes as part of a step of determining chimerism of a treated animal. The kit may also include HLA-mismatched donor stem cells, e.g., allogeneic BMT, mobilized peripheral blood cells, cord blood cells, or hematopoietic cells derived from cultured stem/progenitor cells.

Other features and advantages of the invention will be apparent from the following detailed description, and from the claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

Figure 1:
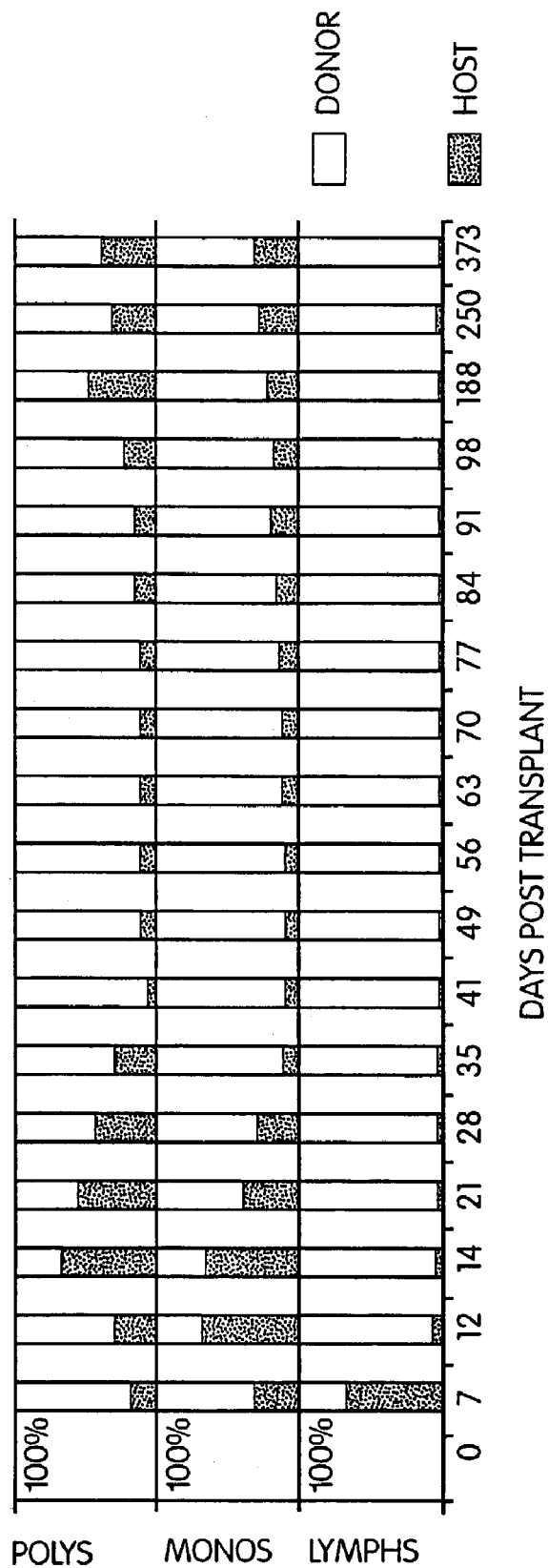
FIG. 1: Time course of mixed WBC chimerism in Patient 1. The percentage of donor (open bar) and host (solid bar) cells in each WBC population is shown over time. Each WBC population is normalized to 100%, so that the proportion of that particular population that is of donor vs. host origin is presented.

DETAILED DESCRIPTION OF THE INVENTION (i) Overview

Bone marrow transplantation (BMT) has previously been limited from its full potential for the treatment of hematologic malignancies, due to the fact that most patients in need of an allogeneic BMT do not have HLA-matched donors available. A major obstacle to further advancement of HLA-mismatched donor BMT following standard myeloablative conditioning therapy for hematologic malignancies has been the occurrence of severe graft-versus-host disease (GVHD) and graft failure.

The present invention provides an approach which can be used in human patients in which lymphohematopoietic graft-versus-host (GVH) reactions, e.g., graft-versus-leukemia or graft-versus-lymphoma, can occur without GVHD. The non-myeloablative conditioning of the subject method permits the generation of mixed hematopoietic chimeras produced across MHC barriers, including, significantly, class II mismatches. The more potent alloresponses generated against MHC disparities compared to those against minor histocompatibility antigens usually elicits severe GVHD, which has been the major impediment to HLA-mismatched BMT (Clift et al. (1987) *Ann Rev Immunol.* 5:43-64. In certain HLA-mismatched BMT described herein, the subject protocols could not completely suppress GVHD, but in many instances it was surprisingly mild and amenable to corticosteroid therapy and the like.

(ii) Definitions

For convenience, certain terms employed in the specification, examples, and claims are collected here.

"Stromal tissue", as used herein, refers to the supporting tissue or matrix of an organ, as distinguished from its functional elements or parenchyma.

"Hematopoietic space", as used herein, refers to a condition created in the bone marrow which promotes engraftment of administered stem cells. In the art, hematopoietic space has often been created by irradiation of the bone marrow with whole body irradiation, but the methods of the invention generally use nonmyeloablative treatments.

"Hematopoietic stem cell", as used herein, refers to a cell, e.g., a bone marrow cell, or a fetal liver or spleen cell, which is capable of developing into all myeloid and lymphoid lineages and by virtue of being able to self-renew can provide long term hematopoietic reconstitution. Purified preparations of hematopoietic cells or preparations, such as bone marrow, which include other cell types, can be used in methods of the invention. Although not wishing to be bound by theory, it is believed that the hematopoietic stem cells home to a site in the recipient. The preparation should include immature cells, i.e., undifferentiated hematopoietic stem cells; these desired cells can be separated out of a preparation or a complex preparation can be administered. E.g., in the case of bone marrow stem cells, the desired primitive cells can be separated out of a preparation or a complex bone marrow sample including such cells can be used. Hematopoietic stem cells can be from fetal, neonatal, immature or mature animals. Stem cells derived from the cord blood of the recipient or the donor can be used in methods of the invention. See U.S. Pat. No. 5,192,553, hereby incorporated by reference, and U.S. Pat. No. 5,004, 681, hereby incorporated by reference.

A "peripheral blood stem cell" is a cell with the potential to produce all the components of blood that is obtained from peripheral blood rather than from bone marrow.

An "immunosuppressive agent", as used herein, is an agent, e.g., a chemical agent, e.g., a drug, which, when administered at an appropriate dosage, results in the inhibition of T cells. Examples of such agents are cyclosporine, FK-506, and rapamycin.

"Thymic or lymph node or thymocytes or T cell", as used herein, refers to thymocytes or T cells which are resistant to inactivation by traditional methods of T cell inactivation, e.g., inactivation by a single intravenous administration of anti-T cell antibodies, e.g., anti-bodies, e.g., ATG preparation.

"Thymic irradiation", as used herein, refers to a treatment in which at least 20, and preferably at least 50, 75, 90, or 95% of the administered irradiation is targeted to the thymus. Whole body irradiation, even if the thymus is irradiated in the process of delivering the whole body irradiation, is not considered thymic irradiation.

"MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes.

The term "histocompatibility" refers to the similarity of tissue between different individuals. The level of histocompatibility describes how well matched the patient and donor are. The major histocompatibility determinants are the human leukocyte antigens (HLA). HLA typing is performed between the potential marrow donor and the potential transplant recipient to determine how close a HLA match the two are. The closer the match the less the donated marrow and the patient's body will react against each other.

The term "human leukocyte antigens" or "HLA", refers to proteins (antigens) found on the surface of white blood cells and other tissues that are used to match donor and patient. For instances, a patient and potential donor may have their white blood cells tested for such HLA antigens as, HLA-A, B and DR. Each individual has two sets of these antigens, one set inherited from each parent. For this reason, it is much more likely for a brother or sister to match the patient than an unrelated individual, and much more likely for persons of the same racial and ethnic backgrounds to match each other.

In hematopoietic transplantation, the word "match" relates to how similar the HLA typing is between the donor and the recipient. The best kind of match is an "identical match". This means that all six of the HLA antigens (2 A antigens, 2 B antigens and 2 DR antigens) are the same between the donor and the recipient. This type of match is described as a "6 of 6" match. Donors and recipients who are "mismatched" at one antigen are considered a "5 of 6" match, and so forth.

The term "allogeneic donor stem cells" refers to cells for transplantation in a subject which are derived from a family member (other than an identical twin) or from an unrelated individual, and as used herein includes cells from the same or different species, the latter being more particularly referred to as "xenogeneic".

"Hematopoietic space-creating irradiation", as used herein, refers to irradiation directed to the hematopoietic tissue, i.e., to tissue in which stem cells are found, e.g., the bone marrow. It is of sufficient intensity to kill or inactivate a substantial number of hematopoietic cells. It is often given as whole body irradiation.

"Thymic space" as used herein, is a state created by a treatment that facilitates the migration to and/or development in the thymus of donor hematopoietic cells of a type which can delete or inactivate host thymocytes that recognize donor antigens. It is believed that the effect is mediated by elimination of host cells in the thymus.

"Tolerance", as used herein, refers to an inhibition of a graft recipient's immune response which would otherwise occur, e.g., in response to the introduction of a nonself MHC antigen into the recipient. Tolerance can involve humoral, cellular, or both humoral and cellular responses. Tolerance, as used herein, refers not only to complete immunologic tolerance to an antigen, but to partial immunologic tolerance, i.e., a degree of tolerance to an antigen which is greater than what would be seen if a method of the invention were not employed. Tolerance, as used herein, refers to a donor antigen-specific inhibition of the immune system as opposed to the broad spectrum inhibition of the immune system seen with immunosuppressants. Tolerance is the ability of the graft to survive in an MHC mismatched or xenogeneic recipient without chronic immunosuppression.

"Inhibiting immune cell activity" refers to reducing the number of active immune cells, e.g., thymocytes, T cells, B cells, or NK cells, preferably donor reactive cells, or precursor donor reactive cells, in a subject. Inhibition can include partial inhibition, or partial reduction (as opposed to total elimination) of the number of active immune cells, e.g., T cells.

The term "relapse" refers to the recurrence of illness after recovery; whereas the term "remission" refers to the disappearance of cancer cells following treatment. Also the period during which this reduction or disappearance of symptoms occur.

"Discordant species combination", as used herein, refers to two species in which hyperacute rejection occurs when a graft is grafted from one to the other. Generally, discordant species are from different orders, while non-discordant species are from the same order. For example, rats and mice are non-discordant concordant species. Concordant species combinations do not exhibit hyperacute rejection. In xenogeneic method of the invention, the donor and recipient (subject) can be a discordant or non-discordant species combination.

"Miniature swine", as used herein, refers to a miniature pig which is preferably wholly or partially inbred at at least one MHC locus. The coefficient of inbreeding of the herd which supplies the miniature swine should be at least, 0.70 and more preferably at least 0.82. The herd from which donor animals are drawn should be homozygous at the SLA genes.

(iii) Exemplary Embodiments

Methods of the invention allow exploitation of the engraftment-promoting and GVL effects of donor T-cells while minimizing GVHD in HLA-mismatched pairs and in xenogeneic methods, allowing many more patients to benefit from hematopoietic stem cell transplantation.

GVL effects are mediated by T-cells and other cell types in allogeneic marrow inocula. While GVL effects are often associated with GVHD, these two phenomena can be dissociated. One strategy for separating these phenomena is the temporal separation of BMT and donor T-cell infusion. Methods of the invention provide initial conditioning, with a mild, relatively non-toxic and non-myeloablative regimen. The combination of a mild conditioning regimen and the recovery time permitted before administration of donor T-cells allows the use of this approach in older patients with chronic hematologic malignancies who are otherwise not considered eligible for BMT.

Because of the high precursor frequency of T lymphocytes reacting to allogeneic MHC molecules, the anti-MHC responses in an allogeneic setting result in much more potent and more rapid GVL responses than are observed for MHC-matched BMT. The presence of single HLA antigen mismatches is associated with increased GVL effects in BMT from related donors. Because of the very potency of these anti-MHC responses, and because of the ubiquity of class I MHC expression, GVHD is a major impediment to the full exploitation of this potentially enormous GVL effect. The greater susceptibility of lymphohematopoietic cells than other host tissues to destruction by MHC-specific donor T-cells may be due to the immediate contact of donor cells with host cells within the lymphohematopoietic system. Additional inflammatory stimuli, such as cytokines induced by myeloablative conditioning treatments may be required to activate endothelial cells and, in combination with activation-induced increased function of T-cell adhesion molecules, permit T-cell adhesion and migration into GVHD target tissues. Unfortunately, the prior art conditioning of patients for allogeneic BMT particularly harsh conditioning, may activate inflammatory stimuli, thus explaining their exquisite sensitivity to the development of GVHD. Methods of the invention avoid GVHD while preserving the strong lymphohematopoietic GVL effects of mismatched allogeneic or xenogeneic donor tissue without causing GVHD, in part, by the use of conditioning regimens that are less toxic and less pro-inflammatory, followed by delayed administration of donor T-cells. Such a delay allows recovery of host immune resistance to GVHD and/or resolution of the conditioning-induced pro-inflammatory state, and hence decreased susceptibility to GVHD. Since the host conditioning used is not myeloablative, this approach is particularly appropriate for the treatment of chronic leukemias, for which immediate curative cytoreduction need not be attempted.

Bone marrow transplantation has not been widely used for the treatment of chronic lymphocytic leukemia (CLL), an incurable and ultimately fatal disease, due largely to the fact that this disease often afflicts older patients who are not considered eligible for allogeneic bone marrow transplantation. Since CLL is a slow-growing leukemia, it is particularly amenable to cure without ablative conditioning when allogeneic T-cells are administered for their GVL effect. Additional chronic hematologic malignancies that often afflict older persons include multiple myeloma, chronic myelogenous leukemia, and low- and intermediate-grade non-Hodgkin's lymphomas are amenable to methods of the invention.

Successful allogeneic bone marrow transplantation is often limited by (1) lack of HLA-matched donor (only 25-30% of patients will have an HLA-phenotypically-identical sibling) and for patients who do undergo an allogeneic BMT, (2) substantial treatment-related mortality, particularly in patents ≧40 years of age, and (3) disease relapse. Methods of the invention expand the availability of transplantation by allowing transplants from HLA-mismatched donors and xenogeneic donors, improve the safety profile of BMT, and enhance the graft-versus-malignancy effects of mismatched transplantation. Methods of the invention provide a number of advantages including: (1.) A moderate dose of cyclophosphamide, a dose of 200 mg/kg, is not myeloablative and is associated with less regimen-related morbidity and mortality than conventional transplant preparative regimens. Post-chemotherapy hematopoietic recovery is expected in approximately 2 weeks following drug administration. While the decreased aggressiveness of the chemotherapy could also mean less tumor cell kill, the decreased cytoreductive effect of chemotherapy will be outweighed by an enhanced graft-versus-malignancy effect. (2.) The non-myeloablative conditioning regimen and the presumably lower likelihood of graft-versus-host disease will allow for treatment of patients of older age than are considered for conventional allogeneic BMT.

Thus, methods of the invention provide for: less toxic conditioning, which induces less host damage and less pro-inflammatory response to conditioning; partial depletion of donor T cells by administration to the subject of T cell inhibiting treatment, e.g., anti-T cell antibodies; and minimization of GVHD by delaying donor leukocyte administration until the pro-inflammatory environment created by conditioning has receded. Methods of the invention allow the use of hematopoietic stem cells from mismatched, or xenogeneic, donors, and thus provide increased GVL activity and increases the number of individuals who can receive hematopoietic stem cell therapy for hematologic malignancies.

Methods of the invention also provide for the treatment of non-neoplastic disorders or a hemoglobinopathies, e.g., sickle cell anemia, aplastic anemia, thalassemia, or similar disorders.

In a preferred embodiment, the invention features, a method of treating a subject e.g., a human, having a hematologic disorder, e.g., a hematologic malignant disorder, e.g., leukemia.

Certain embodiments of the subject methods also feature preparative regimens which minimize or eliminate the need for myeloablative treatment, e.g., hematopoietic space-creating irradiation, especially, preparative whole body irradiation.

One aspect of the present invention provides a method for treating a subject having a hematologic disorder comprising: (i) administering a myeloreductive non-myeloablative treatment to the subject in sufficient amount such that mixed hematopoietic chimerism can be induced in the subject, and (ii) introducing into the subject, allogeneic donor hematopoietic stem cells (donor stem cells) to form chimeric bone marrow in the subject.

In preferred embodiments each of the recited steps is a separate discrete administration or agent.

In methods described herein, the donor can be from the same species as the subject, or from a different species. In allogeneic methods the donor of stem cells and the donor of leukocytes should be the same individuals. In xenogeneic methods, the subject is a mammal, preferably a primate and more preferably a human. The donor mammal can be, by way of example, a swine, e.g., a miniature swine, or a nonhuman primate. In xenogeneic methods the donor of stem cells and the donor of leukocytes need not be the same individual but can be from different individuals which are MHC matched or highly inbred, e.g., inbred miniature swine which are MHC matched.

While not wishing to be bound by theory, the myeloreductive non-myeloablative treatment is believed to prepare the subject for the induction of mixed chimerism and may have a cytoreductive effect on cancer cells. The myeloreductive non-myeloablative treatment should be administered prior to introduction of the donor hematopoietic stem cells, preferably sufficiently prior to the administration of donor hematopoietic stem cells such that if it includes the administration of a chemical agent, the chemical agent will be cleared from the circulatory system, e.g., preferably to a concentration of less than 0.1 of the $EC_{50}$ of the drug for myeloreduction, prior to the administration of donor hematopoietic stem cells.

In certain embodiments, the myeloreductive treatment includes treating the subject, prior to introduction of the donor stem cells, with an cytoreductive agent selected from one or more of alkylating agents (e.g., nitrogen mustards [such as mechloretamine], cyclophosphamide, melphalan and chlorambucil), alkyl sulphonates (e.g., busulphan), nitrosoureas (e.g., carmustine, lomustine, semustine and streptozocine), triazenes (e.g., dacarbazine), antimetabolites (e.g., folic acid analogs such as methotrexate), pyrimidine analogs (e.g. fluorouracil and cytarabine), purine analogs (e.g., fludarabine, idarubicin, cytosine arabinoside, mercaptopurine and thioguanine), vinca alkaloids (e.g., vinblastine, vincristine and vendesine), epipodophyllotoxins (e.g., etoposide and teniposide), antibiotics (e.g., dactinomycin, daunorubicin, doxorubicin, bleomycin, plicamycin and mitomycin), dibromomannitol, deoxyspergualine, dimethyl myleran and thiotepa.

Preferred myeloreductive non-myeloablative agents are alkylating agents, e.g., cyclophosphamide, or fludarabine or similar substances, however, hematopoietic space creating antibodies or drugs, e.g., inhibitors of cell proliferation, e.g., DSG, or an anti-metabolite, e.g. brequinar, or an anti-T cell antibody, e.g., one or both of an anti-CD4 or anti-CD8 antibody can be used as a myeloreductive non-myeloablative agent.

In preferred embodiments, the myeloreductive non-myeloablative treatment is sufficiently mild that at lest 10, and more preferably at least 30, 50, or 75% of the subjects to which it is administered will form mixed chimeras (as opposed to having their bone marrow totally ablated).

In preferred embodiments, immune cell activity, e.g., T cell activity, preferably graft reactive T cell activity, is inhibited in the subject. While not wishing to be bound by theory, the inhibition of T cells is believed to prepare the subject for the induction of mixed chimerism by inhibition of subject T cell activity which would mount an immune response against the donor hematopoietic stem cells and to inhibit donor T cell activity which would mount an immune response against the subject (GVHD).

Numerous methods of inhibiting T cell activity are suitable for use in methods described herein. By way of example, these include:

the administration of anti-T cell antibodies, e.g., an ATG preparation, polyclonal or monoclonal antibody directed against CD4, CD8, or CD2 (an anti-CD2 antibody, e.g., the anti-CD2 monoclonal antibody BTI-322 or a humanized version thereof, or an antibody which overlaps or binds the epitope recognized by BTI-322, are particularly useful);

the administration of an agent, e.g., an antibody, which blocks or otherwise inhibits a pathway, e.g., a costimulatory pathway, of T cell activation (agents, e.g., antibodies, which block the CD28-B7 pathway, e.g., a CTLA4-IgG fusion protein, or agents, e.g., an antibody which blocks the CD40-gp39 pathway, e.g., an anti-gp39 antibody, are particularly suited for use in the method), or generally, by the administration of a treatment which down modulates or otherwise inhibits one or more of the T cell receptor, CD4 co-receptor, CD8 co-receptor or other receptor or co-receptor which promotes T cell activation or maturation;

the administration of an IL-12 receptor protein (functional antagonist, U.S. Ser. No. 5,831,007);

the administration of substituted dihydrobenzofurans, spirobenzofuran-2(3H)-cycloalkanes according to U.S. Ser. No. 5,808,109;

the administeration of anti-asialo antisera;

the administration of an immunosuppressive agent, e.g., a macrolide, e.g., cyclosporine, FK506, or rapamycin; and the administration of thymic irradiation, or other treatment which creates thymic space.

In certain embodiments, the myeloreductive treatment includes treating the subject with an immunosuppressant regimen, prior to introduction of the donor stem cells, in an amount sufficient to prevent rejection of the donor stem cells by the host immune system. For example, such immunosuppressant regimens can include, independently for pre- and post-transplantation is both are carried out, a treatment of the subject which inactivates and/or depletes host T-lymphocytes and/or natural killer (NK) cells in the subject. For example, the immunosuppressant regimen includes treatment with T cell-depleting anti-CD4 and/or CD8 antibodies, such as anti-thymocyte globulin (ATG), OKT3, LO-CD2a, or Minnesota anti-lymphoblast globulin (MALG). Preferably, the immunosuppressant regimen, both before and after transplantation, includes administration of ATG.

In other embodiments, the immunosuppressant regimen includes treatment with one or more of a macrolide immunosuppressant, azathioprine, steroids (e.g., prednisone, methyl prednisolone), or sub-lethal nonmyeloablative irradiation of lymphocyte-containing tissue.

Treatments which inhibit T cell activity can be administered at any time in the course of the method but should not be such that donor T cells will be entirely eliminated. Treatments can be administered prior to, at the same time as, or after, the administration of donor hematopoietic stem cells. Preferably, such treatments are provided both before and after the administration of donor hematopoietic stem cells. Treatment prior to the administration of donor hematopoietic stem cells is believed desirable in that it will condition the subject for the receipt of the donor hematopoietic stem cells. Treatment after the administration of donor hematopoietic stem cells is believed desirable in that it will reduce donor-immune attack on the host and further promote acceptance by the subject of the donor hematopoietic stem cells.

For best results, treatments to inhibit T cell activity, e.g., anti-T cell antibodies or cyclosporine, can be administered repeatedly. E.g., such treatment can be administered one, two, three, or more times prior to donor bone marrow transplantation. Typically, a pre-stem cell treatment, e.g., the administration of antibodies, will be given to the patient about 1, 2, 3, 4, or 5 days prior to stem cell transplantation. It may be desirable to repeat pre-stem cell administrations every 1-5 days until the patient shows excess antibodies in the serum and about 80, 90, or 99% depletion of peripheral T cells and then to perform the stem cell transplantation. Treatments can also be administered one, two, three, or more times after donor hematopoietic stem cell transplantation. Typically, a post-stem cell transplant treatment will be given about 1, 2, 3, 4, or 5 days after bone marrow transplantation.

In preferred embodiments two or more T cell inhibiting modalities or treatments can be combined. In particularly preferred embodiments, an antibody, e.g., an anti-T cell antibody, an immunosuppressive agent, e.g., cyclosporine, and thymic irradiation, are all administered to the subject. An agent can be administered once, or more than once, but the administrations should be short term and not chronic or long term administration. In general, this will mean the treatment is administered for not more than 30, 45, 60, 90, or 120 days, and in many treatments this means administration on 1, 2, 3, 4, 5, or fewer days. Cyclosporine and similar agents will generally be administered for not more than 30, 45, 60, 90, or 120 days. Antibodies will generally be administered for 1, 2, 3, 4, 5, or fewer days.

While not wishing to be bound by theory, the donor hematopoietic stem cells are believed to provide hematologic function, and to induce tolerance to donor antigen, so as to reduce the subject response to any subsequent donor tissue, e.g., a donor leukocyte infusion, which is administered.

In preferred embodiments, mixed chimerism is induced in the subject and the state of mixed chimerism is formed in the absence of hematopoietic space created by space creating irradiation, e.g., whole body irradiation.

In preferred embodiments, donor leukocytes are administered to the subject. While not wishing to be bound by theory, the donor leukocyte administration is believed to provide additional GVL activity—donor leukocytes are believed to further and very effectively reduce the number of cancer cells in the subject. The need for or appropriateness of donor leukocyte administration can be evidenced by a lack of increase in donor chimerism, lack of GVHD symptoms, or incomplete tumor regression. Donor leukocyte administration should be delayed for at least 10, 20, 30, 35 or 60 days after the administration of any myeloreductive non-myeloablative or other space creating treatment. Initial trials showed a delay of about 35 days to be suitable. The donor leukocyte infusion is delayed to avoid introduction of relatively large numbers of donor immune cells into the host during the period in which the space creating treatment has induced pro-inflammatory conditions. Delay allows the host to recover from conditioning and to be less susceptible to GVHD, especially when mismatched donor tissue is used. The donor leukocyte infusion converts the mixed chimeric state of the subject to one which is fully chimeric, but, the graft cell mediated immune attack will be limited to the hematopoietic compartment, thereby minimizing GVHD and maximizing GVL effects.

In preferred embodiments the method includes creating thymic space in the subject. Thymic space can be created, e.g., by irradiating the thymus of the subject, e.g., by administering between 100 and 1,000, more preferably between 300 and 700, e.g., 700 rads, of thymic irradiation, or by administering anti-T cell antibodies in sufficient dose to inactivate thymocytes. Other methods for the creation of thymic space include: the administration of steroids, corticosteroids, brequinar, or an immune suppressant chemical or drug, e.g., rapamycin, cyclosporin, or FK506. An effective treatment should deplete single positive thymocytes to an extent that engraftment and the formation of mixed chimerism is optimized. In preferred embodiments the subject's single positive thymocytes are depleted by at least 20, 40, 60, or 80%. Treatments which result in between 10 and 90% depletion are preferred.

In preferred embodiments the subject does not receive additional treatments which stimulate the release of a cytokine by mature T cells. E.g., the subject should not receive a substance, e.g., a steroid drug, e.g., Prednisone (17,21-dihydroxypregna-1,4-diene-3,11,20-trione), at a dosage or concentration which stimulates the release of a cytokine by mature T cells in the subject. Preferably, the subject is free of such treatment from the time stem cells are first administered until mixed chimerism is established or donor leukocytes administered.

Preferred embodiments include the administration of an agent, e.g., 15-deoxyspergualin, mycophenolate mofetil, brequinar sodium, or a similar agent, which inhibits the production, levels, or activity of antibodies in the subject.

In preferred embodiments, particularly xenogeneic methods, the method includes: inhibiting natural killer cells of the subject preferably prior to introducing donor tissue into the subject, e.g., by introducing into the subject an antibody capable of binding to natural killer cells of the subject.

One source of anti-NK antibody is anti-human thymocyte polyclonal anti-serum. A second anti-mature T cell antibody can be administered as well, which inhibits T cells as well as NK cells. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

In preferred embodiments, the donor stem cells are provided as allogeneic bone marrow, mobilized peripheral blood cells, or cord blood cells. The donor stem cells, in some instances, can be expanded ex vivo for transplantation.

In preferred embodiments, particularly xenogeneic embodiments, the method includes administering donor species stromal cells or administering donor specific growth factors or cytokines, e.g., SCF or GM-SGF. Where the donor is a miniature swine, the method can include administering one or more of swine SCF, swine IL-3, or swine GM-SCF, to the subject. The method can further include the step of administering a first or subsequent dose of a cytokine or growth factor to the subject: when the subject begins to show signs of rejection; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1-2% of the cells.

In preferred embodiments, particularly xenogeneic embodiments, the method includes the step of, preferably prior to hematopoietic stem cell transplantation, inhibiting natural subject antibodies, e.g., by depleting natural antibodies from the blood of the subject. Depletion can be achieved, by way of example, by contacting the subject's blood with an epitope which absorbs preformed anti-donor antibody. The epitope can be coupled to an insoluble substrate and provided, e.g., as an affinity column. E.g., an α1-3 galactose linkage epitope-affinity matrix, e.g., matrix bound linear B type VI carbohydrate, can be used to deplete natural antibodies. Depletion can also be achieved by hemoperfusing an organ, e.g., a liver or a kidney, obtained from a mammal of the donor species. (In organ hemoperfusion antibodies in the blood bind to antigens on the cell surfaces of the organ and are thus removed from the blood.) Other methods for depleting or otherwise inactivating natural antibodies can be used with the methods described herein. For example, drugs which deplete or inactivate natural antibodies, e.g., deoxyspergualin (DSG) (Bristol), or anti-IgM antibodies, can be administered to the recipient of an allograft or a xenograft. One or more of, DSG (or similar drugs), anti-IgM antibodies, and hemoperfusion, can be used to deplete or otherwise inactivate subject natural antibodies in methods of the invention.

In preferred embodiments: the donor of the hematopoietic stem cell and the donor leukocytes is the same individual. In other preferred embodiments, particularly xenogeneic embodiments, the donor of the hematopoietic stem cell and the donor leukocytes can be different individuals, e.g., different individuals which are MHC identical.

Although methods of the invention generally reduce or eliminate the need for myeloablative conditioning some embodiments include the step of, prior to hematopoietic stem cell transplantation, creating hematopoietic space for the induction of mixed chimerism by irradiating the subject with low dose, e.g., less than 400, preferably less than 300, more preferably less than 200 or 100 rads, whole body irradiation to partially deplete the bone marrow of the subject. The level of such treatment will be very substantially lower than that used in lethal conditioning. As is discussed herein, this treatment can be reduced or entirely eliminated.

The method can include a further step of treating the subject with an immunosuppressant regimen, after introduction of the donor stem cells, in an amount sufficient to prevent a graft-versus-host response mediated by the donor stem cells.

Preferably, the pre-transplantation conditioning includes administration of ATG and cyclophosphamide, and thymic irradiation. Preferably the cyclophosphamide, or other cytoreductive agents, are substantially cleared from the patient so as not inhibit proliferation of the transplanted stem cells.

An important use of the subject method is for allogeneic transplantation of donor stem cells which are mismatched, with respect to the subject, at one or more class II HLA antigens.

Another important use of the subject method is for allogeneic transplantation of donor stem cells which are mismatched, with respect to the subject, at two or more HLA antigens (either class I or II or both).

In several embodiments, particularly where little, and preferably no GVHD is detected post-transplantation (e.g., at 35 days or longer), the subject method includes the further step of administering allogeneic donor leukocytes to the subject after introduction of the donor stem cells. The administration of donor leukocytes should be delayed sufficiently from the time of any hematopoietic space creating treatment such that the level of pro-inflammatory cytokines induced by the space creating treatment has subsided sufficiently to reduce or substantially eliminate GVHD from the donor leukocytes.

The subject method can also include the management of GVHD responses post-transplantation by administration of immunosuppressants, or by use of engineered stem cells which give rise to small molecule ablatable T cells or other hematopoietic cells. See, for example, U.S. Pat. No. 5,834,266.

Thus, in one preferred embodiment, the subject method comprises: (i) identifying a patient having a neoplastic hematopoetic disorder, (ii) administering a myeloreductive treatment to the subject in sufficient amount such that mixed hematopoietic chimerism can be induced in the subject, and (iii) introducing into the subject, allogeneic donor hematopoietic stem cells (donor stem cells) to form stable mixed chimeric bone marrow in the subject.

In another preferred embodiment, the subject method comprises: (i) identifying a patient having a neoplastic hematopoetic disorder, (ii) administering a myeloreductive treatment to the subject in sufficient amount such that mixed hematopoietic chimerism can be induced in the subject, and (iii) introducing into the subject, allogeneic donor hematopoietic stem cells (donor stem cells) to form mixed chimeric bone marrow in the subject, wherein the donor stem cells are mismatched, with respect to the patient, at one or more class II HLA antigens.

In still another preferred embodiment, the subject method comprises: (i) identifying a patient having a neoplastic hematopoetic disorder, (ii) administering a myeloreductive treatment to the subject in sufficient amount such that mixed hematopoietic chimerism can be induced in the subject, and (iii) introducing into the subject, allogeneic donor hematopoietic stem cells (donor stem cells) to form mixed chimeric bone marrow in the subject, wherein the donor stem cells are mismatched, with respect to the patient, at two or more HLA antigens, e.g., class I and/or class II.

In yet another preferred embodiment, the subject method comprises: (i) identifying a patient having a neoplastic hematopoetic disorder, (ii) administering a myeloreductive treatment to the subject in sufficient amount such that mixed hematopoietic chimerism can be induced in the subject, (iii) introducing into the subject, allogeneic donor hematopoietic stem cells (donor stem cells) to form mixed chimeric bone marrow in the subject, and (iv) administering a post-transplantation immunosuppression regimen for suppressing or depleting T-cells in the transplanted donor stem cells.

In yet another preferred embodiment, the subject method comprises: (i) identifying a patient having a neoplastic hematopoetic disorder, (ii) administering a pre-transplantation conditioning to the subject in sufficient amount such that mixed hematopoietic chimerism can be induced in the subject, which pre-transplantation conditioning includes treating the cells with cyclophosphamide, ATG and thymic irradiation in an amount sufficient to reduce rejection of transplanted donor stem cells; and (iii) introducing into the subject, allogeneic donor hematopoietic stem cells (donor stem cells) to form mixed chimeric bone marrow in the subject, and (iv) administering ATG to the subject post-transplant for suppressing or depleting T-cells in the transplanted donor stem cells.

In another embodiment, the subject method includes:
administering a myeloreductive non-myeloablative treatment, e.g., an alkylating agent, e.g., cyclophosphamide, or fludarabine or a similar substance, to the subject in sufficient amount such that mixed hematopoietic chimerism can be induced in the subject, preferably without myeloablative treatment such as whole body irradiation;

preferably, inhibiting immune cell, e.g., T cell activity, in the subject;

introducing into the subject, donor hematopoietic stem cells, preferably mismatched allogeneic or xenogeneic hematopoietic stem cells, e.g., introducing donor bone marrow, to form chimeric bone marrow in the subject (as is discussed below, if a sufficiently large number of donor hematopoietic stem cells are introduced the myeloreductive non-myeloablative (hematopoietic space creating) treatment can be minimized or eliminated); and optionally, administering to the subject, donor leukocytes, thereby treating the disorder, e.g., relieving or alleviating one or more symptoms of the disorder. The administration of donor leukocytes should be delayed sufficiently from the time of any hematopoietic space creating treatment such that the level of pro-inflammatory cytokines induced by the space creating treatment has subsided sufficiently to reduce or substantially eliminate GVHD from the donor leukocytes.

In still another embodiment the method of treating a hematologic malignancy includes the following:
administering cyclophosphamide to the subject in sufficient amount such that mixed chimerism can be induced in the subject without myeloablative treatment;

inhibiting T cell activity in the subject by administering thymic irradiation;

inhibiting T cell activity in the subject by administering an anti-T cell antibody, and a short course of cyclosporine both before and after the administration of donor hematopoietic stem cells;

introducing into the subject, allogeneic donor hematopoietic stem cells; and optionally, administering to the subject, donor leukocytes.

In still another embodiment the method is used to treat a hemoglobinopathy, e.g., sickle cell anemia, aplastic anemia, thalassemia, or similar disorder, and includes the following:
administering a myeloreductive non-myeloablative treatment, e.g., an alkylating agent, e.g., cyclophosphamide, or fludarabine or a similar substance, to the subject in sufficient amount such that mixed hematopoietic chimerism can be induced in the subject, preferably without myeloablative treatment such as whole body irradiation;

preferably, inhibiting immune cell, e.g., T cell activity, in the subject; and introducing into the subject, donor hematopoietic stem cells, e.g., introducing donor bone marrow, to form chimeric bone marrow in the subject (as is discussed below, if a sufficiently large number of donor hematopoietic stem cells are introduced the myeloreductive non-myeloablative (hematopoietic space creating) treatment can be minimized or eliminated), to thereby treat the disorder. In the treatment of non neoplastic disorders, and generally when conversion to full donor chimerism is not required, the administration of donor leukocytes can be omitted.

Methods of the invention can be used to treat hematologic disorders. A hematologic disorder is a disorder in which there is a malfunction in the subject's hematopoietic cells, e.g., the hematopoietic stem cells, which can be treated by replacing or supplementing the subject's hematopoietic stem cells. Hematologic disorders include disorders having unwanted cell proliferation, e.g., hematologic cancers, e.g., hematopoietic and lymphoid malignancies, e.g., leukemia, e.g., chronic lymphocytic leukemia (CLL) and other chronic hematologic malignancies, including multiple myeloma, chronic myelogenous leukemia, and low- and intermediate-grade non-Hodgkin's lymphomas. Hematologic disorders also include, non-neoplastic disorders and hemoglobinopathies, e.g., sickle cell anemia, aplastic anemia, thalassemia, and similar disorders.

As used herein, myeloablative, refers to a treatment in which death, due to marrow failure, in a significant number of recipients, will occur if hematopoietic stem cell transplantation is not given.

As used herein, non-myeloablative, refers to a treatment which kills marrow cells but will not, in a significant number of recipients, lead to death from marrow failure.

As used herein, myeloreductive, refers to a treatment which causes cytopenia or anemia.

Subject, as used herein, refers to a mammal, e.g., a human.

Allogeneic Methods

The methods described herein can be used where, as between the donor and recipient, there is any degree of mismatch at MHC loci or other loci which influence graft rejection. Unlike conventional bone marrow transplantation, mismatch is desirable in methods of the invention, as mismatch promotes GVL effects. Methods of the invention can be used where, as between allogeneic donor and recipient, there is a mismatch at at least one MHC locus or at at least one other locus that mediates recognition and rejection, e.g., a minor antigen locus. With respect to class I and class II MHC loci, the donor and recipient can be: matched at class I and mismatched at class II; mismatched at class I and matched at class II; mismatched at class I and mismatched at class II; matched at class I, matched at class II. Mismatched, at class I or II, can mean mismatched at one or two haplotypes. Mismatched at MHC class I means mismatched for one or more MHC class I loci, e.g., in the case of humans, mismatched at one or more of HLA-A, HLA-B, or HLA-C. Mismatched at MHC class II means mismatched at one or more MHC class II loci, e.g., in the case of humans, mismatched at one or more of a DP $\alpha$, a DP$\beta$, a DQ $\alpha$, a DQ $\beta$, a DR $\alpha$, or a DR $\beta$. In any of these combinations other loci which control recognition and rejection, e.g., minor antigen loci, can be matched or mismatched. It is preferable that there is mismatch at at least one class I or class II locus and, more preferably, mismatch at one class I and one class II locus.

The methods described herein for inducing tolerance to an allogeneic antigen or allogeneic graft can be used where, as between the donor and recipient, there is any degree of reactivity in a mixed lymphocyte assay, e.g., wherein there is no, low, intermediate, or high mixed lymphocyte reactivity between the donor and the recipient. In preferred embodiments mixed lymphocyte reactivity is used to define mismatch for class II, and the invention includes methods for performing allogeneic grafts between individuals with any degree of mismatch at class II as defined by a mixed lymphocyte assay. Serological tests can be used to determine mismatch at class I or II loci and the invention includes methods for performing allogeneic grafts between individuals with any degree of mismatch at class I and or II as measured with serological methods. In a preferred embodiment, the invention features methods for performing allogeneic grafts between individuals which, as determined by serological and or mixed lymphocyte reactivity assay, are mismatched at both class I and class II.

In preferred embodiments the donor and the subject are not related, e.g., the donor is not a sibling, the offspring of, or the parent of the recipient.

Xenogeneic Methods

Methods of the invention can use xenogeneic donors. E.g., when the subject is a human, the donor can be a non-human primate or a swine, preferably a miniature swine.

Hematopoietic Stem Cells

Methods of the invention require the introduction of donor hematopoietic stem cells. Administration and engraftment of the donor stem cells converts the subject to a mixed chimera. Because donor hematopoietic stem cells are at a competitive disadvantage to subject hematopoietic stem cells, it is often desirable to create hematopoietic space in the donor, in order to promote engraftment of the donor cells. Methods of the invention use mild non-myeloablative methods, e.g., the administration of cyclophosphamide, to create hematopoietic space. However, if a sufficient number of donor cells are administered, the subject need not receive space-creating treatment. See e.g., U.S. patent application Ser. No. 08/855,705, filed May 8, 1997, hereby incorporated by reference. Thus, other methods of the invention administer a sufficient number of donor hematopoietic stem cells such that the creation of space, even with mild methods, is not required. This approach is particularly useful in xenogeneic methods, especially those in which very large numbers of donor hematopoietic stem cells are available, e.g., when the donor or donors are inbred miniature swine.

The number of donor stem cells administered to the recipient can be increased by either increasing the number of stem cells provided in a particular administration or by providing repeated administrations of donor stem cells.

Repeated stem cell administration can promote engraftment and mixed chimerism in recipients. In preferred embodiments, particularly xenogeneic embodiments, multiple administrations of donor stem cells can be provided. A second (or other subsequent) administration of hematopoietic stem cell can provided: at least two days, one week, one month, or six months after the previous administration of stem cells; when tumor regression is below desired levels; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1-2% of the cells; or generally, as is needed to maintain tumor regression.

When multiple stem cell administrations are given one or more of the administrations can include a number of donor hematopoietic cells which is at least twice, is equal to, or is at least 75, 50, or 25% as great as, the number of bone marrow cells found in an adult of the recipient species; include a number of donor hematopoietic stem cells which is at least twice, is equal to, or is at least 75, 50, or 25% as great as, the number of bone marrow hematopoietic stem cells found in an adult of the recipient species. Such large numbers are useful in reducing or eliminating the need for space creating treatment, even mild treatments.

The method of introducing stem cells may be altered, particularly by (1) increasing the time interval between administering hematopoietic stem cells and space creating treatment or leukocyte infusion; (2) increasing the amount of hematopoietic stem cells injected; (3) varying the number of hematopoietic stem cell injections; (4) varying the method of delivery of hematopoietic stem cells; (5) varying the tissue source of hematopoietic stem cells, e.g., a fetal liver cell suspension may be used; or (6) varying the donor source of hematopoietic stem cells. Although hematopoietic stem cells derived from the leukocyte donor are preferable, hematopoietic stem cells may be obtained from other individuals or species, or from genetically-engineered inbred donor strains, or from in vitro cell culture.

Sources of Cells for Allogeneic Stem Cell Transplantation

A living human donor can provide about $7.5 \times 10^8$ bone marrow cells/kg. Methods of the invention can include the administration of at least 2 or 3 times this number (per kg) especially when it is desired to reduce or eliminate space creating treatments, and preferably at least 10, 15, or 20 times this number. Such large numbers are useful in reducing or eliminating the need for space creating treatment, even mild treatments. The requisite numbers of bone marrow cells can be provided by the ex vivo expansion or amplification of human stem cells. Ex vivo expansion is reviewed in Emerson, 1996, Blood 87:3082, hereby incorporated by reference. Methods of ex vivo expansion are described in more detail in Petzer et al., 1996, Proc. Natl. Acad. Sci. USA 93:1470; Zundstra et al., 1994, BioTechnology 12:909; and WO 95 11692 Davis et al., all of which are hereby incorporated by reference. Sources of hematopoietic stem cells include bone marrow cells, mobilized peripheral blood cells, and when available cord blood cells.

The hematopoietic system reconstituting cells administered to the recipient can, in one example, be present in a source population of between $0.2 \times 10^8$ and $4.0 \times 10^8$, or ranges there between, donor bone marrow cells/kg of the recipient's body weight. The bone marrow cells can be obtained from the donor by standard bone marrow aspiration techniques known in the art. Bone marrow cells are removed from the donor by placing a hollow needle into the marrow space and withdrawing a quantity of marrow cells by aspiration.

Alternatively, the hematopoietic system reconstituting cells administered to the recipient can, in one example, be present in a source population of between $1.0 \times 10^8$ and $40 \times 10^8$, or ranges there between, donor cytokine mobilized peripheral blood stem cells/kg of recipient's body weight. Peripheral blood cells can be obtained from the donor, for example, by standard phlebotomy or apheresis techniques. Phlebotomy is performed by placing a hollow needle into a vein and withdrawing a quantity of whole blood using aspiration or gravity. Apheresis is performed in a similar manner to phlebotomy except the whole blood is anticoagulated and then separated into the constituent formed cellular elements by centrifugation. The mononuclear cell fraction is retained and the remaining plasma and other cellular elements (red blood cells, granulocytes, platelets) are returned to the donor by intravenous infusion.

Peripheral blood stem cells can be cytokine mobilized by injecting the donor with hematopoietic growth factors such as Granulocyte colony stimulating factor (G-CSF), granulocyte-monocyte colony stimulating factor (GM-CSF), stem cell factor (SCF) subcutaneously or intravenously in amounts sufficient to cause movement of hematopoietic stem cells from the bone marrow space into the peripheral circulation. The hematopoietic reconstituting cells can also be derived from fetal or embryonic human tissue that is processed and/or cultured in vitro so as to increase the numbers or purity of primitive hematopoietic elements.

In addition, the hematopoietic system reconstituting cells administered to the recipient can also be hematopoietic system cells that have been enriched from the source population. The source population can be either donor bone marrow cells or donor peripheral blood cells. The hematopoietic system reconstituting cells can be enriched from the source population by selecting cells that express the CD34 antigen, using combinations of density centrifugation, immuno-magnetic bead purification, affinity chromatography, and fluorescent activated cell sorting, known to those skilled in the art (Baum et al., (1992) *Proc. Natl. Acad. Sci. U.S.A.* 89:2804-8; Lansdorp et al., (1990) *J Exp. Med.* 172:363-6; Sato et al., (1991) *Blood* 78:967-74; Smith et al., (1991) *Blood* 77:2122-8; Udomsakdi et al., (1991) *Exp. Hematol* 19:338-42; Udomsakdi et al., (1992) *Blood* 80:2513-21.

The treated mononuclear cells and hematopoietic system reconstituting cells are typically administered to the recipient in a pharmaceutically acceptable carrier by intravenous infusion. Carriers for these cells can include but are not limited to solutions of phosphate buffered saline (PBS) containing a mixture of salts in physiologic concentrations.

Sources of Cells for Xenogeneic Stem Cell Transplantation

In the case of inbred donor animals, e.g., inbred miniature swine, very large numbers of stem cells are available, as the number which can be supplied is not limited by the number which can be harvested from a single donor.

In the case where the recipient is a primate, e.g., a human, and the donor is a swine, e.g., a miniature swine, $7.5 \times 10^9$ or more, and preferably, between $7.5 \times 10^9$ and $15 \times 10^{10}$, swine bone marrow cells/kg can be administered, though this will vary with factors such as the intensity of the preparative regimen and the health of the individual recipient. Such large numbers are useful in reducing or eliminating the need for space creating treatment, even mild treatments. As discussed herein, these cells can be provided in more than one administrations.

Treatment of Hematologic Cancers

The following provides a protocol for the treatment of a human subject having a hematologic cancer in a preliminary clinical setting. The protocol describes the major components of the treatment, the therapy to be provided to the patient, pre- and post-treatment evaluation, and supportive care likely to be needed in the course of the treatment. This protocol is exemplary of an embodiment of the invention and is not limiting.

The treatment consists of four major components:
1. Conditioning therapy, e.g., with cyclophosphamide 200 mg/kg and thymic irradiation (7 Gy) and BMT.
2. GVHD prophylaxis, e.g., with anti-thymocyte globulin (ATG) and cyclosporine.
3. Post-transplant supportive care (antibiotics, transfusional support, hemopoietic growth factors, etc.)
4. Donor leukocyte infusions (days +35, +56).
5. Thymic irradiation except patients who have received previous mediastinal radiation therapy.

Scheme of therapy is as follows:

| Day | Treatment | | |
|---|---|---|---|
| −6 | Cyclophosphamide 50 mg/kg | | |
| −5 | Cyclophosphamide 50 mg/kg | | |
| −4 | Cyclophosphamide 50 mg/kg | | |
| −3 | Cyclophosphamide 50 mg/kg | | |
| −2 | | ATG 15 mg/kg | |
| −1 | Thymic irradiation (7 Gy) | ATG 15 mg/kg | CYA 5 mg/kg IV |
| 0 | Bone marrow infusion | | CYA 5 mg/kg IV |
| +1 | | ATG 15 mg/kg | |
| +4 | | | CYA 3 mg/kg IV |
| +15 | | | CYA 12 mg/kg PO |
| +30 | | | CYA 12 mg/kg PO |
| +35 | Donor leukocyte infusion | | |
| +56 | Donor leukocyte infusion | | |

Treatment modalities referred to in the scheme of therapy are as follows:

A. Cyclophosphamide (Cytoxan™)
1. Dosage: cyclophosphamide is administered at a dosage of 50 mg/kg on days −6, −5, −4, and −3. cyclophosphamide is dissolved in distilled water and administered over 60 minutes. Dose should be calculated based on actual or ideal body weight, whichever is less. Volume of distilled water to be used is 250 ml for adults.
2. Sedation, antinausea: Dexamethasone, Diphenhydramine, Lorazepan and Granisetron prior to cyclophosphamide.
3. Because of a 20% incidence of hemorrhagic cystitis, the following plan of fluid administration and management is recommended for prevention:
   a. IV hydration fluids for adults should be at 3000 ml/m$^2$/24 hours, beginning 4 hours prior to cyclophosphamide administration. Typically the hydration fluid is $D_5NS$+20 mEq KCL/liter. This fluid should be continued for 24 hours after the last dose of cyclophosphamide.
   b. MESNA at a dose of 15 mg/kg will be administered 15 minutes before and 3, 6, and 9 hours after cyclophosphamide (with an additional dose 24 hours after the fourth IV dose).
   c. Additional KCL and $NaHCO_2$ may be needed depending on patient's electrolyte and uric acid status.
4. Toxicity and complications
   a. Nausea and vomiting. Variable but usually well controlled with anti emetics.
   b. Uric acid nephropathy. A potential problem that is easily prevented by high urine flow plus alkalinization and allopurinol.
   c. Fluid retention. cyclophosphamide causes an antidiuretic effect usually counteracted by furosemide administration. Careful physical examination and accurate weights three times a day should be able to detect fluid overload early.
   d. Cardiomyopathy. cyclophosphamide causes nonspecific ST changes at this dose level and at total doses ≧200 mg/kg (7.6 grams/m$^2$) fatal cardiac failure due to hemorrhagic necrosis can occur. cyclophosphamide is contraindicated in patients with pre-existing cardiac disease. Patients should receive an EKG on admission, on each day cyclophosphamide is given, and 1 day following cyclophosphamide.
   e. Diarrhea. May be a problem and should be treated symptomatically with Tincture of Opium (dose is 1-3 drops/dose) or Immodium. Stool volume loss should be replaced with $D_5W$ and an appropriate electrolyte solution.
   f. Hemorrhagic cystitis. Approximately 50% of patients will have some hernaturia at this dose level, but is usually not symptomatic or severe unless there is inadequate diuresis. An occasional patient will get severe cystitis despite adequate urine flow.
   g. Alopecia. The patient should be told of hair loss prior to drug administration.
   h. Skin rash. 10-20% of patients develop a diffuse maculopapular rash 24-72 hours following cyclophosphamide. The rash usually resolves in 24-48 hours.
   i. Anemia. Hematocrit decrements out of proportion to cessation of production will occur at this dose, presumably due to hemolysis.
   j. Electrolyte imbalance. This should be anticipated and daily electrolytes followed.

B. Anti-thymocyte Globulin (ATG; ATGAM™, Upjohn Co.)
1. Dosage: ATG is prepared in 1 liter of normal saline and is given at a dose of 15 mg/kg over 10-12 hours on days −2, −1, and +1. The dose of ATG will be based on ideal or actual body weight, whichever is less.
2. Skin Testing
   a. All patients will receive an intradermal skin test (0.1 ml of a 1 mg/ml solution) and observed for 30 minutes for the presence of a wheat/flare reaction. If positive, an alternative treatment plan may be considered by the principal investigator. Benadryl 50 mg IV, epinephrine (1:1000 solution) and hydrocortisone 100 mg IV will be available at the bedside in the event of a possible allergic reaction.
3. Pre-Medication
   a. All patients will receive dexamethasone 10 mg IV Q 12 hrs on days −2, −1, and +1. Each ATG infusion will be preceded by Benadryl IV and Tylenol 650 mg.
4. Toxicities
   a. Allergic reactions (including anaphylaxis), rash, fevers, rigors, arthralgias, myalgias, dyspnea, serum sickness (including rash, arthritis, proteinuria), hypotension, tachycardia.

C. Cyclosporine (Sandimmune™, Sandoz Co.)
1. Cyclosporine is commercially available and is administered either in an intravenous form (mixed in 250 ml of distilled water), or an oral olive oil based solution, or in capsule form (100 and 25 mg capsules).
2. All patients will receive cyclosporine starting on day −1 at a dose of 5 mg/kg/day intravenously infused over a period of 20 hours daily. The dose will be reduced to 3 mg/kg/day on day +4 until the patient is able to tolerate p.o. cyclosporine (on or after day +15 post-transplant) at a dose of 6 mg/kg twice daily. Cyclosporine will be dose adjusted on the following criteria:
   a. Cyclosporine levels: an attempt will be made to keep cyclosporine dose levels within the therapeutic range (between 250-350 mg/ml by monoclonal assay). Given an association between low cyclosporine levels and the development of acute GVHD, attempts will be made to keep the level in the high normal range particularly during the first 4 weeks post transplant.
   b. Dose reduction should be considered for significant renal dysfunction (e.g. greater than a 50% increase from baseline serum creatinine level particularly accompanied by a high cyclosporine level).
   c. Careful attention should be given to cyclosporine levels and renal function in the face of hepatic disease, given the extent of hepatic metabolism of cyclosporine.
   d. In the absence of acute GVHD, cyclosporine will be tapered and discontinued by day +30 post-transplant.

D. Thymic Irradiation
1. 7 Gy of thymic irradiation will be administered in a single dose on day −1.
2. Possible toxicities of thymic irradiation include bone marrow suppression, nausea, vomiting, esophagitis, pneumonitis, pericarditis and secondary malignancy.

E. Bone Marrow Infusion
1. Allogeneic bone marrow will be rapidly infused intravenously without a filter as soon as possible after harvest.
   a. Acute toxicities:
      1. Pulmonary emboli. Marrow and fat emboli may rarely cause a transient alveolar capillary block and temporary administration of $O_2$ may be necessary.
      2. Hypotension.
      3. Volume overload.

F. Donor Leukocyte Infusion(s)
1. Donor peripheral blood mononuclear cells will be collected via leukophoresis on days +35 and +56 post-transplant. Based on established anti-tumor efficacy of $1\times10^7$/kg T-cells in CML and reduced risk of GVHD with this dose compared with $\geq 5\times10^7$/kg T-cells (34), an initial infusion (day +35) of $1\times10^7$/kg CD3+ T-cells will be performed. If no GVHD is observed and fully donor (greater than or equal to 90%) chimerism has not been established, or if there is evidence of persistent malignancy, a second dose of $10^7$/kg T-cells will be infused on day +56 post-transplant.
2. Recipient risks of receiving donor leukocyte infusions include acute and chronic GVHD and marrow aplasia.

Evaluation

The following protocol can be used to evaluate prospective recipients.
   A. Pre-transplant
   1. History. A complete history with full details of the patient's previous treatment and response will be obtained, including:
      a. Patient exposure to steroids, radiation and antileukemic drugs (total dosage of each antileukemic drug and when given).
      b. Previous or current fever, infections and antibiotic treatment.
      c. Previous CNS involvement and other evidence of extramedullary leukemia.
      d. Clinical picture at initial presentation including Karnofsky score.
      e. Prior immunologic and cytogenetic studies of the patient's leukemic cells.
   2. Clinical evaluation (all measurements in metric units).
      a. A complete physical examination.
      b. Chest and other radiographs as clinically indicated.
      c. Marrow aspiration and biopsy for staging and cytogenetics.
      d. EKG
      e. Dental consult and evaluation of status of teeth and gums.
      f. Lumbar puncture(s) for determination of presence of CNS leukemia and administration of IT therapy for patients with intermediate to high grade non-Hodgkin's lymphoma.
      g. Pulmonary consult for baseline respiratory studies, with room air arterial blood gas.
   3. The following laboratory data should be obtained:
      a. ABO and Rh typing and two-way red cell crossmatch with donor.
      b. HLA typing of patient and available family members and potential platelet donors.
      c. Hepatitis B surface antigen, HCV, HSV, CMV, HIV and HTLV-1 antibody determinations for patient and marrow donors.
      d. Cultures of blood, stool, urine, nose, and throat for potential pathogenic bacteria, viruses and fungi.
      e. CBC, reticulocyte count, chem 20 and toxoplasma titers. 10 ml serum (2 dry red tops) and 20 cc of heparinized blood (2 green tops) for immunologic studies to Dr. Spitzer.
      f. Lymphoma or leukemia cells, from marrow or peripheral blood, if available, to be frozen in DMSO for later immunologic studies (send to Dr. Spitzer).

The following protocol can be used to monitor patients who receive treatment with methods of the invention.
   B. Evaluation during conditioning and the first 100 days post-transplantation
   1. Daily CBC until granulocytes and platelets are self-sustaining; at least three times weekly until discharge, and then once or twice weekly until 100 days post-transplant.
   2. Daily chemistry profile for the first 3 weeks, then as clinically indicated, but at least once weekly.
   3. Marrow aspiration and biopsy on day 28 and 100 post-transplant.
   4. Chest x-ray every 7 days.
   5. Serum to serum bank (10 ml clotted blood to Dr. Spitzer) every 7 days.
   6. Viral, bacterial and fungal cultures weekly or when clinically indicated or as specified in other protocols until discharge, then as clinically indicated.
   7. EKG daily during and 1 day after last dose of cyclophosphamide.
   8. Daily weights.
   9. Respiratory function tests per attending.
   10. Blood for CSP levels every Monday or as per attending (7 mg lavender EDTA tube).
   11. Screening studies for chronic GVHD on day 100 (per Dr. Spitzer).
   12. Chimerism studies: see study parameter (section XI).
   C. Evaluation following 100 days post-transplant
   1. Monthly evaluations here for local patients and by referring physicians for patients who live elsewhere for one year following engraftment.
   2. Monthly CBC and chem 20 for 6 months. Marrow aspiration as indicated clinically or required by other protocols.
   3. Periodic studies as per other specific protocols.
   4. Complete evaluation every 6 months for 2 years, then annually.

Supportive Care

The following outlines supportive care which may be appropriate.
   A. Access to vessels. All patients will have placement of a silastic indwelling triple lumen central venous catheter (or have dual double lumen catheters) on or before admission.
   B. Hyperalimentation (HAL). Some patients will require hyperalimentation soon after conditioning. Given the hepatotoxic potential of HAL, caloric intake will be adjusted to provide approximately 50 to 75% of the calculated need.
   C. Transfusions.
   1. Indication. Platelets are transfused to prevent bleeding and an attempt will be made to keep the circulating platelet level $>20\times10^9$/L at all times. Packed red blood cells will be transfused to maintain a hematocrit of $\geq 25\%$.
   2. Single donor apheresis platelet products containing a minimum equivalent of 6 units of random donor platelets will be preferentially used.
   3. Patients will have their CMV serostatus determined prior to conditioning therapy. CMV negative patients will receive CMV negative blood products as available.
   4. All platelet and red cell transfusions will be white blood depleted using third generation leukocyte filters.
   5. Irradiation. All products are irradiated with 2500 rad (from a 137/Cs irradiator) prior to infusion to inactivate lymphocytes and prevent a transfusion associated GVHD.
   6. Problems.
      a. Alloimmunization. Patients frequently become refractory to mismatched platelets due to alloimmunization to HLA and platelet antigens. For practical purposes, this is established by failure to demonstrate an adequate increment 60 minutes after a 4-6 unit equivalent transfusion. If non-family platelets are required and the patient is immunized to random donors, attempts should be made to locate an unrelated platelet donor with no HLA antigens in excess of the recipient. Mismatched platelets may be harmful in the presence of alloimmunization, with chills, fever and a drop in circulating platelet and neutrophil levels.

b. Consumption. These patients have complicated problems leading to rapid consumption of platelets, and the distinction between this and alloimmunization is often difficult. Patients who demonstrate an adequate post-transfusion increment but have rapid disappearance of platelets are assumed to have consumption and will be given more frequent platelet transfusions.

c. Allergic reaction. Chills, fever, and hives occasionally occur despite adequate circulation of platelets. These are presumed to be allergic reactions to antigens other than HLA or platelet antigens and can be controlled with diphenhydramine. However, if associated with no increment or with a decrement, these reactions are probably associated with alloimmunization to the transfused platelets and that donor should not be used again.

D. Management of infections. Principals of infection prophylaxis and treatment will vary according to the spectrum of organisms and their antibiotic sensitivity and concurrent infection management/antibiotic clinical trials. General principals of infection management will include:

1. reduced bacteria diet
2. HEPA filtered or LAF protective isolation
3. Oral Ofloxacin 400 mg BID, from admission until ANC is $>0.5 \times 10^9$/L for antibacterial prophylaxis.
4. Acyclovir 250 mg/m$^2$ IV or PO q8h days −1 until discharge for HSV prophylaxis.
5. Fluconazole PO or IV days −1 until ANC is $>0.5 \times 10^9$/L for antifungal prophylaxis.
6. Broad spectrum antibiotics for fever (T$\geq$100$^5$) in the face of neutropenia with continuation of antibiotics until ANC is $>0.5 \times 10^9$/L. Antibiotic choice will vary but will usually consist of vancomycin and a third generation cephalosporin (e.g. ceftazidime) or imipenem. Aminoglycosides should be avoided if possible in view of potential synergistic renal toxicity with CSP and IL2.
7. For CMV prophylaxis/therapy:
   a. CMV negative blood products for CMV seronegative recipients.
   b. IVIG 500 mg/kg/week days −8 through +28, then every other week through day +100.
   c. DHPG for positive CMV culture or positive antigen assay.

These procedures may be employed in combination, as described, or in part These procedures are designed to synergistically prevent the problem of GVHD while maximizing the GVL effect of donor tissue.

(iv) Exemplification

The invention now being generally described will be more readily understood by reference to the following examples which are included merely for purposes of illustration of certain aspects and embodiments of the present invention, and are not intended to limit the invention.

EXAMPLE 1

Mixed Lymphohematopoietic Chimerism Following a Non-Myeloablative Conditioning Regimen and Allogeneic Bone Marrow Transplant (BMT)

Five patients with chemotherapy (n=5) and radiation (n=2) refractory non-Hodgkin's lymphoma were treated with cyclophosphamide (Cy) 50 mg/kg daily×4 (days −6 through −3), anti-thymocyte globulin 30 mg/kg (days −2, −1, +1) thymic irradiation 700 cGy×1 (n=3) (day −1) and HLA genotypically identical (n=2), phenotypically identical (n=1), or 2 antigen mismatched donor BMT (day 0). Intravenous cyclosporine (CYA) was given beginning on day −1 with conversion to p.o. CYA when tolerated. Donor leukocytes (DLI) were given on days +35, (10$^7$/kg CD3+ cells) and +56 (5×10$^7$/kg CD3+ cells) if no GVHD was present. Median patient age was 30 (range 20-45) years. All patients had disease progression during salvage chemotherapy or radiation therapy. Toxicities have included reversible Cy cardiotoxicity (n=1), and capillary leak syndrome coincident with engraftment (n=4). Median times to ANC >0.5 and platelets >20K have been 16 (range 13-17) and 16 (range 8 to 91+) days. Chimerism analyses of weekly peripheral blood samples and pre-BMT, day +28, and day +100 bone marrow aspirate samples have been performed by variable number of tandem repeat sequence (VNTR) analysis (HLA matched BMT) or flow cytometry (HLA mismatched BMT). In recipients of HLA-matched marrow (n=3) mixed chimerism was seen in all three. One patient had conversion to full donor chimerism following DLI and developed grade III GI GVHD. One patient had $\leq$10% donor cells; at day +35 he had no detectable donor cells. No donor cells were detectable after a subsequent DLI. The third patient has 50-70% donor cells on day +28 with grade II cutaneous GVHD. In the two recipients of HLA-2 antigen mismatched marrow, >90% donor lymphoid chimerism was seen within 2 weeks of BMT coincident with grade II or III GVHD. In one patient gradual conversion to donor myeloid (neutrophils and monocytes) chimerism was observed. In the other patient stable "split" lymphohematopoietic chimerism is present (>90% donor lymphoid, >80% host myeloid). All patients are alive at a median of 103 days (range 3y-122 days) following BMT. Four of five patients are clinically disease-free at the present time. Mixed lymphohematopoietic chimerism is achievable following a novel non-myeloablative conditioning regimen and HLA-matched or mismatched BMT. Dramatic anti-tumor responses have been seen in the majority of cases.

EXAMPLE 2

Activation-Induced Cell Death in Donor TCR Transgenic T Cells with Known Host Antigen Specificity The expansion and elimination of donor T cell receptor (TCR) transgenic T cells with known host antigen specificity was examined in a murine BMT model. In 2C T-cell receptor transgenic mice (H-2$^b$ on B6 background), a large fraction of T cells express CD8 and the αβ T-cell receptor from the cytotoxic T lymphocyte clone 2C, which specifically recognizes the MHC class I antigen L$^d$ (Sha, W. C. et al., Nature 335, 271-274 1988). Lethally irradiated, L$^{d+}$ BALB/c (H-2$^d$) mice were transplanted with 10×10$^6$ spleen cells from anti-L$^d$ 2C TCR-transgenic B6 mice. By 4 days after BMT, the numbers of 2C CD8 cells in the spleens of BALB/c recipients had increased 14-16 fold over the number administered. However, they had drastically decreased to similar numbers to those administered by day 7. By 3-color FCM using 7-AAD (amino-actinomycin-D) for DNA staining, we found that an increasing fraction (4-11%) of GVH-reactive 2C CD8 cells in spleens of 2→BALB/c recipients underwent apoptotic cell death between days 4 and 7 after BMT, coincident with the observed decrease in absolute numbers of 2C CD8 cells in recipients' spleens. In addition, 2C CD8 cells showed reduced expression of 2C TCR and CD8 on days 4, 7, and 21. They also demonstrated anergy upon stimulation with anti-αβTCR and 1B2 (anti-2C clonotypic mAb) mAbs at these time points. 2C CD8 cells remaining on day +21 expressed the CD45RB$^{low}$ CD44$^{high}$ Me114$^{low}$, previously activated/memory phenotype. Clinically, the recipients did not show any evidence of acute GVHD, and all animals survived beyond day 80, although some of them exhibited mild chronic GVHD. The early clonal expansion of 2C CD8 cells, down-regulation of CD8 and TCR, anergy and deletion of 2C CD8 cells via activation-induced cell death, are all the consequences of a vigorous immune response. However, this marked monoclonal expansion of GVH-reactive 2C CD8 cells is incapable of inducing severe acute or subacute GVHD.

EXAMPLE 3

Mixed Lymphohematopoietic Chimerism and Graft-vs-Lymphoma Effects are Achievable in Adult Recipients Following Non-Myeloablative Therapy and HLA-Mismatched Donor Bone Marrow Transplantation Methods: Five patients with refractory non-Hodgkins lymphomas underwent BMT from two of six HLA antigen-mismatched (in the GVH direction) donors. Conditioning included pre-transplant cyclophosphamide, pre- and post-transplant anti-thymocyte globulin (ATG), and pre-transplant thymic irradiation. Additional GVHD prophylaxis consisted only of cyclosporin A.

Findings: Four of four evaluable patients engrafted, and mixed hematopoietic chimerism was established, with donor lymphoid predominance and varying levels of myeloid chimerism. Two patients are in GVHD-free complete and partial clinical remissions at 460 and 103 days post-BMT, respectively.

Interpretation: This is the first demonstration that mixed chimerism can be intentionally induced in adult recipients of HLA-mismatched BMT. Moreover, this has been achieved using a non-myeloablative conditioning regimen. The striking anti-lymphoma responses seen in several patients suggest that allogeneic BMT can have potent immunotherapeutic benefits in the absence of myeloablative conditioning.

Introduction

Patients with chemo- and radio-resistant non-Hodgkins lymphomas (NHL) have a very poor prognosis. HLA-identical allogeneic or autologous bone marrow transplantation has led to durable remissions in only 0-23% of patients[1,2]. However, animal studies have shown that MHC-disparate bone marrow transplants can mediate anti-tumor effects that greatly exceed those achieved with MHC-matched BMT[3,4]. The potential of HLA-mismatched bone marrow transplantation as immunotherapy for hematologic malignancies has not yet been exploited, largely because of the high incidence of intractable GVHD[5] and of potentially lethal failure of marrow engraftment associated with standard ablative conditioning regimens[6-8].

Studies in rodents have shown that mixed hematopoietic chimeras produced across MHC barriers are resistant to the development of GVHD, even when lymphohematopoietic GVH reactions are intentionally induced that convert mixed chimeras to fully allogeneic chimeras[9] (M.-G. Wang and M. Sykes, unpublished data). Murine mixed chimeras produced with a non-myeloablative conditioning regimen of T cell-depleting mAbs, cyclophosphamide (CP), and thymic irradiation (TI), can be converted into full donor chimeras without developing GVHD when donor lymphocytes are administered 5 weeks post-BMT. We have now adapted the mixed chimerism approach for use in humans with hematologic malignancies, using CP for both cytoreduction of malignancy and as an adjunct to host immunosuppression with anti-thymocyte globulin and TI. We show here that cytoreductive, immunosuppressive, but non-myeloablative conditioning administered to patients with refractory hematologic malignancies can induce stable mixed chimerism with potent graft-versus-lymphoma effects.

Patients and Methods

Patients

The five patients described herein were enrolled at the Massachusetts General Hospital in a trial involving non-myeloablative conditioning therapy followed by allogeneic BMT, under the auspices of an MGH Subcommittee for Human Studies-approved protocol. Eligibility criteria included chemotherapy-refractory hematologic malignancy, ECOG performance status of 2 or less, age of 65 years or less and adequate organ function (as specified by the protocol). A less than three of six HLA antigen-mismatched related donor was required. Patients and donors were typed using standard serological techniques for HLA-A and B, and SSOP- or SSP-based analyses for HLA-DR.

The characteristics of the HLA-mismatched allogeneic transplant recipients are listed in Table 1. All five had intermediate- to high-grade non-Hodgkins lymphomas that were refractory to chemotherapy ± radiotherapy, and received transplants from two of six (A, B, or DR) HLA antigen-mismatched (in the GVH direction) donors.

Conditioning and Transplantation

Conditioning therapy consisted of intravenous cyclophosphamide (CP) 50 mg/kg/d (with dosing based on actual or ideal body weight, whichever was less) on days −6 through −3, thymic irradiation (700 cGy) on day −1 in patients who had not received previous mediastinal radiation therapy (n=2), and anti-thymocyte globulin (ATG) 30 mg/kg/d (n=2) or 15 mg/kg/d (n=2) on days −2, −1, and +1 (Patients 1 through 4), or 15 mg/kg/d on days −1, +1, +3, +5 (Patient 5). Dexamethasone was used at a dose of 20 mg/d prior to each dose of CP and at a dose of 10 mg twice daily with each dose of ATG. Intravenous cyclosporine, 5 mg/kg daily, was given on day −1 until day +4, when it was reduced to 3 mg/kg/d. When oral medication was tolerated, cyclosporine was changed to an oral route at a dose of 6 mg/kg q12h.

Donor bone marrow was procured under anesthesia by standard techniques. A target number of 3×10$^8$/kg nucleated cells was sought. In the case of minor ABO incompatibility (n=1), plasma was removed from donor marrow prior to transplantation. In the case of major ABO-incompatibility (n=1), red blood cells were depleted from the donor marrow using a CS-3000 cell separator (Baxter-Fenwal, Round Lake, Ill.).

Analyses of Chimerism

Flow cytometry (FCM) was used for analysis of white blood cells stained with FITC-labeled anti-HLA class I allele-specific mAbs (One Lambda, Inc.; Canoga Park, Calif.) specific for the HLA type of the patient (HLA-Bw4 or A9) or the donor (HLA-A3). These mAbs were used in combination with PE-, PerCP- or APC-conjugated antibodies to the human lymphocyte differentiation antigens CD3, CD4, CD8, CD19, and CD56 (Becton Dickinson). Staining, flow cytometer calibration and analysis was performed with standard techniques[10] on approximately 50,000 cells per analysis tube.

In four of the five recipients, analysis of minisatellite variable number of tandem repeats (VNTR) or short tandem repeat (STR) markers[11;12] were also able to distinguish donor and host. Donor or recipient bands were detectable in mixtures containing as little as 1% of the DNA from the donor or recipient, respectively.

Erythroid chimerism was determined in Patient 1 (recipient blood group A, donor O) by the gel test method of Lapierre[13], using Micro Typing Systems (MTS) (Pompano Beach, Fla.) buffered gel cards with anti-A mAb and anti-H lectin to agglutinate type A and type O RBC, respectively. The sum of $A^+$ and $H^+$ RBC totaled approximately 100%, indicating that all RBC typed as being of either donor or host origin.

RESULTS

Clinical Outcomes

The clinical courses of the five HLA-mismatched patients in our trial are summarized in Table 2. The patient with the longest follow-up (Patient 1) is described in detail. This 20-year-old male presented with a left neck mass in May 1996, followed two months later by rigors and night sweats. Biopsy of the mass established the diagnosis of non-Hodgkins lymphoma, diffuse large cell type. Extensive cervical and mediastinal lymphadenopathy with pulmonary involvement and a pericardial effusion were present, indicating stage IVB disease. An initial partial response to cyclophosphamide, doxorubicin, vincristine and prednisone (CHOP) chemotherapy was followed by progression of cervical lymphadenopathy during the sixth cycle. The patient's cervical disease progressed through subsequent chemotherapy with etoposide, cisplatin, cytosine arabinoside, and methyl-prednisolone (ESHAP) and ifosfamide, carboplatin and etoposide (ICE) and local irradiation (3000 cGy). He was entered on this protocol, and on May 7, 1997 he underwent allogeneic bone marrow transplantation from his HLA-mismatched brother (2 of 6 HLA antigen mismatch [HLA-A and -B] in the GVH direction and one antigen mismatch [HLA-B] in the HVG direction). In the second week post-transplant, an engraftment syndrome (fever and fluid retention) and grade II acute GVHD (skin and gastrointestinal tract involvement) developed, and responded promptly to corticosteroid therapy. A measurable decline in the size of his neck mass was evident immediately following chemotherapy. The mass subsequently regressed completely over a period of weeks following transplantation. Restaging at 100 days post-transplant confirmed that he was in a partial remission. Steroids were discontinued approximately six months post-transplant, as the patient had only minimal cutaneous chronic GVHD. Low dose oral cyclosporine was continued. Approximately seven months post-transplant, an IgG warm antibody-mediated autoimmune hemolytic anemia and thrombocytopenia developed. Though initially responsive to oral corticosteroids, hemolytic anemia became exacerbated at 9 months, necessitating splenectomy, which showed no evidence of lymphoma upon pathological examination. The thrombocytopenia and hemolytic anemia resolved, and corticosteroid therapy was tapered. The patient is currently in complete remission from his lymphoma 15 months post-BMT, with no evidence of GVHD. Staging evaluations that included CT scans and bone marrow biopsies at seven months and one year post-transplant confirmed his complete remission status.

Because of the significant GVHD that developed in Patients 1 through 4, Patient 5, who was 51 years old, received a modified protocol that included less pre-transplant and more post-transplant ATG (15 mg/kg on days −1, +1, +3 and +5). Although grade II GVHD, manifested as fever, skin rash, and elevated liver enzymes, developed in the second week, the patient responded well to corticosteroids, which have been tapered without recurrence of GVHD. Staging at 100 days showed that he is in complete clinical remission.

Engraftment and Establishment of Mixed Chimerism

These data are summarized for all five patients in Table 2. Leukopenia and thrombocytopenia occurred within 9 days post-BMT. Leukocyte engraftment (ANC>500/mm3) occurred between 10 and 17 days post-BMT in all evaluable patients. Sustained recovery of platelets (to >20,000/mm$^3$) occurred at 9 to 72 days post-transplant in three patients. Patient 2 was still platelet transfusion-dependent at the time of her death on day 117. One patient died of pulmonary hemorrhage on day 12, before engrafting.

Figure 2:
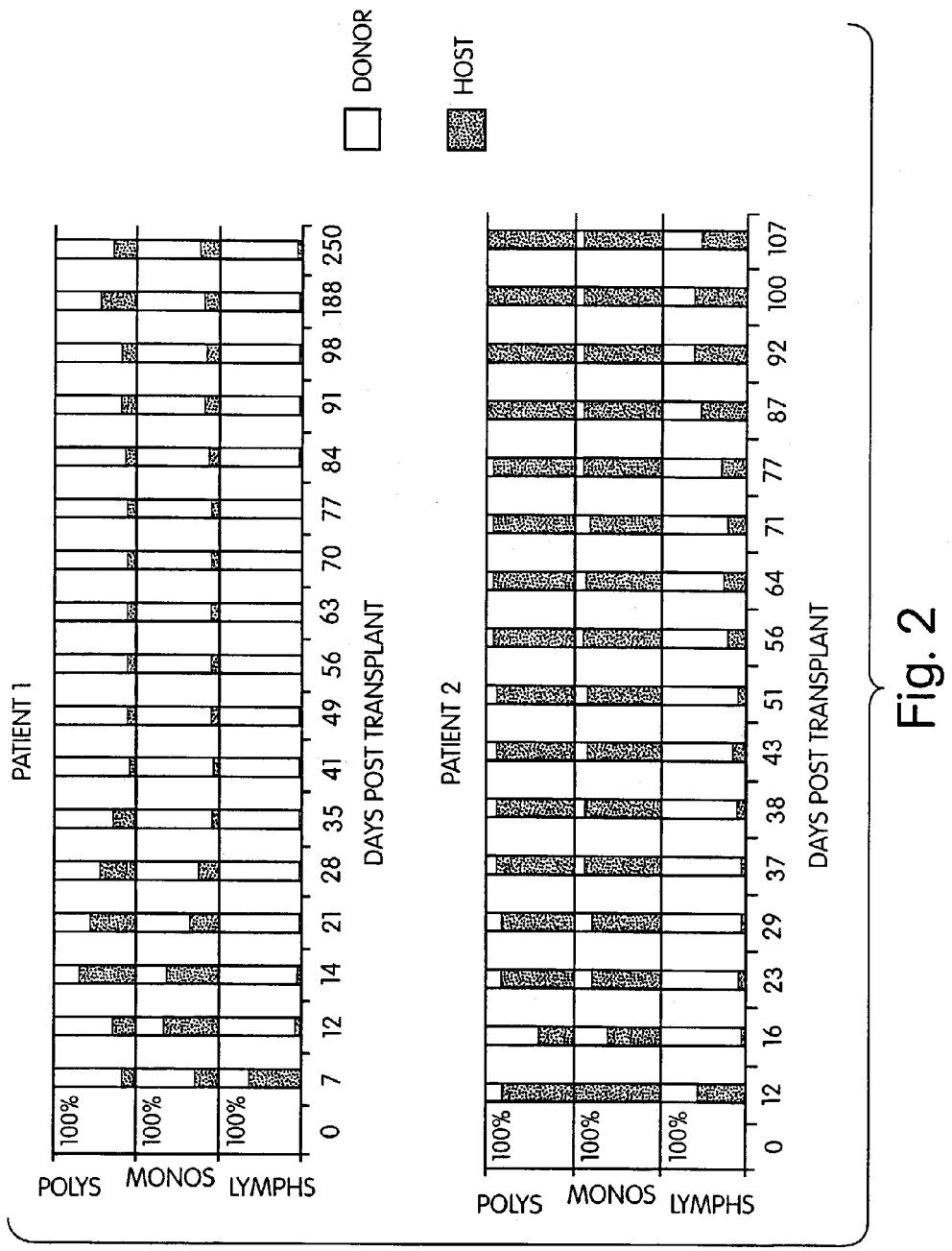
FIG. 2: Mixed chimerism in WBC of Patient 1 one year post-BMT. Lymphocyte, monocyte and granulocyte gates are shown on the forward scatter (FSC)×side scatter (SSC) contour plot, and staining patterns with anti-HLA-A9 mAb are shown for lymphocytes (right top panel), monocytes (right middle panel) and granulocytes (right lower panel). The donor was HLA-A9-negative, whereas the host was A9-positive. The bars above the histograms denote the populations considered to be HLA-A9-negative.

Chimerism was assessed by FCM analysis of WBC beginning 8 to 12 days post-BMT. All patients showed varying proportions of donor cells among lymphocytes, monocytes and neutrophils at the first time point tested (not shown), and at the time of last follow-up (Table 2). The time course for chimerism in these three lineages in Patient 1 is presented in FIG. 1. Mixed chimerism has been sustained for at least one year, when 71% of monocytes, 62% of granulocytes, and 99% of lymphocytes were donor-derived (FIG. 2). T cells and NK cells were >98% donor-derived, whereas B cells were 33% host-derived and 67% donor-derived. Donor erythrocytes were detectable beginning at 6 to 8 weeks post-BMT, and increased to about 80% of RBC by 9 months post-BMT. A marrow aspirate obtained one year post-BMT contained 73% donor and 27% host cells among the non-erythroid elements.

FCM analyses of Patients 1 through 4 relied on the use of HLA allele-specific mAbs that could specifically identify host, but not donor cells. The presence of donor cells, for which specific HLA allele-specific mAbs were not available, was verified in Patients 1, 2, and 4 by VNTR or STR analyses, which showed distinct donor bands in each sample.

DISCUSSION

Our studies demonstrate that lasting multilineage mixed hematopoietic chimerism, with high levels of donor reconstitution, can be induced across extensive HLA barriers in adult BMT recipients. Moreover, we show that such chimerism can be achieved in recipients conditioned with a non-myeloablative regimen, without severe or intractable GVHD, and that it is associated with striking anti-tumor responses in patients with advanced, refractory non-Hodgkins lymphomas.

Induction of mixed chimerism across MHC barriers has not, to our knowledge, been previously reported in adult humans. Lasting mixed chimerism in adults has been achieved across MHC barriers only in rodents[14;15]. Mixed chimerism has been induced in dogs, but only in MHC-identical donor-recipient pairs[16], and transient mixed chimerism has been achieved across MHC barriers in monkeys after non-myeloablative conditioning[17].

The lack of myeloablation by the ATG/cyclophosphamide/thymic irradiation conditioning protocol used here is demonstrated by the survival of recipient hematopoietic progenitors that are capable of contributing to myeloid, lymphoid and erythroid lineages. Furthermore, in a similarly-conditioned recipient of an HLA-matched transplant (data not shown), secondary failure of donor hematopoiesis was not associated with significant cytopenias, due to the ability of surviving host hematopoietic progenitors to sustain multilineage hematopoiesis.

Transplantation of HLA-mismatched marrow in myeloablated humans has been associated with a significant incidence of failure of engraftment[6], which can be reduced with the use of additional chemotherapy and immunotherapy[18;19]. Our results suggest that specific targeting of host immune resistance with the combination of cyclophosphamide, anti-thymocyte globulin, and thymic irradiation can effectively overcome host resistance to HLA-mismatched marrow engraftment, despite being less toxic than conventional myeloablative regimens.

In several recent studies of non-myeloablative conditioning regimens containing purine analogs in combination with other chemotherapeutic agents, high levels of donor reconstitution were achieved in recipients of HLA-matched sibling marrow. Although tumor responses were obtained primarily in patients with either conventional-risk malignancies or with chemosensitive disease in these studies, they are consistent with our own data showing that BMT can provide immunotherapy without host myeloablation[20-22]. However, matched unrelated donor marrow failed to engraft in two of two patients in one of these studies[23], suggesting that the host conditioning may be less immunosuppressive than that used in our protocol, in which marrow mismatched at one or two of six HLA antigens in the host-vs-graft direction engrafted in all four cases.

Despite studies suggesting a graft-versus-lymphoma effect for allogeneic BMT in non-Hodgkins lymphomas, patients with chemoresistant disease have a very poor prognosis[2;22;24-27]. Striking anti-tumor responses were achieved in several of our patients, despite the fact that they had very advanced, chemoresistant and even radioresistant, refractory disease. Two of the four evaluable patients are in complete and partial remissions at 460 and 103 days, respectively, and a third patient showed no evidence of disease progression at the time of death from aspergillosis on day 117. Since the only chemotherapy included in our protocol was cyclophosphamide, to which the patients all had prior exposure, the anti-tumor responses seen in our study implicate a potent immunotherapeutic effect of the donor marrow inoculum. Although longer follow-up and larger series of patients will be required to determine the potency and curative potential of this new approach to the treatment of non-Hodgkins lymphomas, the anti-tumor responses observed suggest that these may be superior to those achievable with conventional lethal TBI/cyclophosphamide and HLA-matched or closely-matched BMT. This might occur because of the more potent alloresponses directed against MHC alloantigens than against minor histocompatibility antigens, which have led to enhanced GVL effects in rodent studies[3;4]. In addition, the presence of host-derived professional antigen-presenting cells in mixed chimeras could be associated with enhanced GVL effects for other reasons, perhaps related to their ability to efficiently present host alloantigens that are shared by tumor cells.

The more potent alloresponses generated against MHC disparities compared to those against minor histocompatibility antigens usually elicits severe GVHD, which has been the major impediment to HLA-mismatched BMT[5]. The patients described here developed GVHD, but in several patients it was surprisingly mild and amenable to corticosteroid therapy. GVHD prophylaxis consisted of cyclosporine plus a single post-transplant (day +1) treatment with ATG in four patients, and in the fifth patient, whose GVHD was also well-controlled with corticosteroids, an increased proportion of the conditioning ATG was given post-transplant rather than pre-transplant. Less severe host conditioning[28;29] and the initial presence of host hematopoietic elements[30 31] have both been shown to reduce the severity of GVHD in rodents. Larger patient series will determine whether or not our new regimen will allow the routine performance of HLA-mismatched BMT without unacceptable GVHD.

References Cites in Example 2

1. Ratanatharathon V, Uberti J, Karanes C, et al. Prospective comparative trial of autologous versus allogeneic bone marrow transplantation in patients with non-Hodgkin's lymphoma. *Blood* 1994; 84: 1050-1055.
2. Jones R J, Ambinder R F, Piantadosi S, Santos G W. Evidence of a graft-versus-lymphoma effect associated with allogeneic bone marrow transplantation. *Blood* 1991; 77:649
3. Aizawa S, Sado T. Graft-versus-leukemia effect in MHC-compatible and -incompatible allogeneic bone marrow transplantation of radiation-induced, leukemia-bearing mice. *Transplantation* 1991; 52: 885-889.
4. Sykes M, Sachs D H. Genetic analysis of the anti-leukemic effect of mixed allogeneic bone marrow transplantation. *Transplant. Proc.* 1989; 21: 3022-3024.
5. Clift R A, Storb R. Histoincompatible bone marrow transplants in humans. *Ann. Rev. Immunol.* 1987; 5: 43-64.
6. Anasetti C, Amos D, Beatty P G, et al. Effect of HLA compatibility on engraftment of bone marrow transplants in patients with leukemia or lymphoma. *New Engl. J. Med.* 1989; 320: 197-204.
7. O'Reilly R J, Collins N H, Kernan N, et al. Transplantation of marrow depleted of T cells by soybean lectin agglutination and E-rosette depletion: major histocompatibility complex-related graft resistance in leukemic transplant recipients. *Transplant. Proc.* 1985; 17: 455
8. Fleischhauer K, Kernan N A, O'Reilly R J, Dupont B, Yang S Y. Bone marrow-allograft rejection by T lymphocytes recognizing a single amino acid difference in HLA-B44. *New Engl. J. Med.* 1990; 323: 1818-1822.
9. Sykes M, Sheard M A, Sachs D H. Graft-versus-host-related immunosuppression is induced in mixed chimeras by alloresponses against either host or donor lymphohematopoietic cells. *J. Exp. Med.* 1988; 168: 2391-2396.
10. Preffer F I. Diagnostic cytometry. In: Colvin R B, Bhan A K, McCluskey R T, eds. Diagnostic Immunopathology, 2 ed. New York: Raven Press, 1993: 725-749.
11. Schwartz D W M, Glock B, Jungl E M, Mayr W R. Strategy to detect chimerism in allogeneic bone marrow transplant recipients by PCR-amplification fragment length polymorphism analysis of microsatellite polymorphisms. *Vox Sang.* 1995; 68: 139-143.
12. Nakao S, Nakasumi T, Chuhjo T, et al. Analysis of late graft failure after allogeneic bone marrow transplantation: detection of residual host cells using amplification of variable number of tandem repeats. *Bone Marrow Transplant.* 1992; 9: 107-111.
13. Lapierre Y, Rigal D, Adam J, et al. The gel test: A new way to detect red cell antigen-antibody reactions. *Transfusion* 1990; 30: 1091-1113.
14. Ildstad S T, Sachs D H. Reconstitution with syngeneic plus allogeneic or xenogeneic bone marrow leads to specific acceptance of allografts or xenografts. *Nature* 1984; 307(5947): 168-170.
15. Sharabi Y, Sachs D H. Mixed chimerism and permanent specific transplantation tolerance induced by a non-lethal preparative regimen. *J. Exp. Med.* 1989; 169: 493-502.

16. Storb R, Yi C, Wagner J L, et al. Stable mixed hematopoietic chimerism in DLA-identical littermate dogs given sublethal total body irradiation before and pharmacological immunosuppression after marrow transplantation. *Blood* 1997; 89: 3048-3054.
17. Kawai T, Cosimi A B, Colvin R B, et al. Mixed allogeneic chimerism and renal allograft tolerance in cynomologous monkeys. *Transplantation* 1995; 59: 256-262.
18. Henslee-Downey P J, Abhyankar S H, Parrish R S, et al. Use of partially mismatched related donors extends access to allogeneic marrow transplant. *Blood* 1997; 89: 3864-3872.
19. Henslee-Downey P J, Parrish R S, Macdonald J S, et al. Combined in vitro and in vivo T lymphocyte depletion for the control of graft-versus-host disease following haploidentical marrow transplant. *Transplantation* 1996; 61: 738-745.
20. Giralt S, Estey E, Albitar M, et al. Engraftment of allogeneic hematopoietic progenitor cells with purine analog-containing chemotherapy: Harnessing graft-versus-leukemia without myeloablative therapy. *Blood* 1997; 89: 4531-4536.
21. Slavin S, Nagler A, Naparstek E, et al. Nonmyeloablative stem cell transplantation and cell therapy as an alternative to conventional bone marrow transplantation with lethal cytoreduction for the treatment of malignant and nonmalignant hematologic diseases. *Blood* 1998; 91: 756-763.
22. Khouri I F, Keating M, Korbling M, et al. Transplantlite: Induction of graft-versus-malignancy using fludarabine-based nonablative chemotherapy and allogeneic blood progenitor-cell transplantation as treatment for lymphoid malignancies. *J. Clin. Oncol.* 1998; 16: 2817-2824.
23. Giralt S, Gajewski J, Khouri I, et al. Induction of graft-vs-leukemia (GVL) as primary treatment of chronic myelogenous leukemia. *Blood* 1997; 90: 418a (Abstract)
24. Lundberg J H, Hansen R M, Chitambar C R, et al. Allogeneic bone marrow transplantation for relapsed and refractory lymphoma using genotypically HLA-identical and alternative donors. *J. Clin. Oncol.* 1991; 9: 1848
25. Chopra R, Goldstone A H, Pearce R, et al. Autologous versus allogeneic bone marrow transplantation for non-Hodgkin's lymphoma: A case-controlled analysis of the European Bone Marrow Transplantation Group Registry Data. *J. Clin. Oncol.* 1992; 10:1690
26. Ratanatharathorn V, Uberti J, Karanes C, et al. Prospective comparative trial of autologous versus allogeneic bone marrow transplantation in patients with non-Hodgkin's lymphoma. *Blood* 1994; 84: 1050
27. Verdonck L F, Dekker A W, Lokhorst H M, Petersen E J, Nieuwenhuis H K. Allogeneic versus autologous bone marrow transplantation for refractory and recurrent low-grade non-Hodgkin's lymphoma. *Blood* 1997; 90: 4201-4205.
28. Sprent J, Schaefer M, Gao E, Korngold R. Role of T cell subsets in lethal graft-versus host disease (GVHD) directed to class I versus class II H-2 differences. I.L3T4+ cells can either augment or retard GVHD elicited by Lyt-2+ cells in Class I-different hosts. *J. Exp. Med.* 1988; 167: 556-569.
29. Xun C Q, Thompson J S, Jennings C D, Brown S A, Widmer M B. Effect of total body irradiation, busulfan-cyclophosphamide, or cyclophosphamide conditioning on inflammatory cytokine release and development of acute and chronic graft-versus-host disease in H-2-incompatible transplanted SCID mice. *Blood* 1994; 83: 2360-2367.
30. Ildstad S T, Wren S M, Bluestone J A, Barbieri S A, Stephany D, Sachs D H. Effect of selective T cell depletion of host and/or donor bone marrow on lymphopoietic repopulation, tolerance, and graft-vs-host disease in mixed allogeneic chimeras (B10+B10·D2 →B10). *J. Immunol.* 1986; 136: 28-33.
31. Sykes M, Chester C H, Sachs D H. Protection from graft-versus-host disease in fully allogeneic chimeras by prior administration of T cell-depleted syngeneic bone marrow. *Transplantation.* 1988; 46: 327-330.

(v) Other Embodiments

As an alternative or adjunct to hemoperfusion, host antibodies can be depleted by administration of an excess of hematopoietic cells.

Stromal tissue can be introduced prior to hematopoietic cell transplant, e.g., BMT. It may be varied by: (1) administering the fetal liver and thymus tissue as a fluid cell suspension; (2) administering fetal liver or thymus stromal tissue but not both; (3) placing a stromal implant into other encapsulated, well-vascularized sites, or (4) using adult thymus or fetal spleen as a source of stromal tissue.

An anti-CD2 antibody, preferably a monoclonal, e.g., BTI-322, or a monoclonal directed to a similar or overlapping epitope, can be used in addition to or in place of any anti-T cell antibodies (e.g., ATG) in any method referred to herein.

Methods of preparing the recipient for transplant of hematopoietic stem cells may be varied. For instance, recipient may undergo a splenectomy. The latter would preferably be administered prior to the non-myeloablative regimen, e.g., at day −14.

(vi) Incorporation by Reference

All of the above-cited references and publications are hereby incorporated by reference.

(vii) Equivalents

Those skilled in the art will recognize, or be able to ascertain using no more than routine experimentation, many equivalents of the specific embodiments of the invention described herein. Such equivalents are intended to be encompassed by the following claims.

Other embodiments are within the following claims.

What is claimed is:

1. A kit for reducing graft versus host disease (GVHD) in a transplant recipient having a neoplastic hematological disorder comprising at least one cytoreductive agent; an anti-CD2 antibody, or antigen-binding fragment thereof, wherein the anti-CD2 antibody is BTI-322 produced by the hybridoma deposited under ATCC number HB-11423; and an agent which blocks a CD28-B7 costimulatory pathway of T cell activation or a CD40-gp39 costimulatory pathway of T cell activation.

2. The kit of claim 1, wherein the cytoreductive agent is selected from the group consisting of alkylating agents, alkyl sulphonates, nitrosoureas, triazenes, antimetabolites, pyrimidine analogs, purine analogs, vinca alkaloids, epipodophyllotoxins, antibiotics, dibromomannitol, deoxysperguialine, dimethyl myleran and thiotepa.

3. The kit of claim 2 wherein the alkylating agent is cyclophosphamide.

4. The kit of claim 2 wherein the alkylating agent is melphalan.

5. The kit of claim 2 wherein the alkyl sulphonates is busulphan.

6. The kit of claim 2 wherein the purine analog is selected from the group consisting of fludarabine, idarubicin, cytosine arabinoside, mercaptopurine, and thioguanine.

7. The kit of claim 2 wherein the antibiotic is selected from the group consisting of dactinomycin, daunorubicin, doxorubicin, bleomycin, plicamycin and mitomycin.

8. The kit of claim 1, further comprising a pharmaceutically acceptable carrier.

9. The kit of claim 1, wherein the agent which blocks a costimulatory pathway of T cell activation is a CTLA4-IgG fusion protein.

10. The kit of claim 1, wherein the agent which blocks a costimulatory pathway of T cell activation is an agent which blocks the CD28-B7 pathway.

11. The kit of claim 1, wherein the agent which blocks a costimulatory pathway of T cell activation is an agent which blocks the CD40-gp39 pathway.

12. The kit of claim 1, wherein the agent which blocks a costimulatory pathway of T cell activation is an antibody.

13. A kit for reducing graft versus host disease (GVHD) in a transplant recipient having a hematological disorder comprising cyclophosphamide and an anti-CD2 antibody, or antigen-binding fragment thereof, wherein the antibody is BTI-322 produced by the hybridoma deposited under ATCC number HB-11423.

* * * * *